(12) United States Patent
Decker et al.

(10) Patent No.: US 11,141,145 B2
(45) Date of Patent: Oct. 12, 2021

(54) DEVICES AND METHODS FOR SECURING A TISSUE ANCHOR

(71) Applicant: Edwards Lifesciences Corporation, Irvine, CA (US)

(72) Inventors: Steven Eric Decker, Anaheim, CA (US); Matthew Michael Becerra, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 92 days.

(21) Appl. No.: 16/107,718

(22) Filed: Aug. 21, 2018

(65) Prior Publication Data

US 2019/0059876 A1 Feb. 28, 2019

Related U.S. Application Data

(60) Provisional application No. 62/550,361, filed on Aug. 25, 2017.

(51) Int. Cl.
*A61B 17/04* (2006.01)
*A61F 2/24* (2006.01)
(Continued)

(52) U.S. Cl.
CPC ........ *A61B 17/0401* (2013.01); *A61B 17/064* (2013.01); *A61B 17/068* (2013.01);
(Continued)

(58) Field of Classification Search
CPC .... A61F 2/0045; A61F 2/0811; A61F 2/2445; A61F 2/2466; A61F 2002/0072;
(Continued)

(56) References Cited

U.S. PATENT DOCUMENTS 5,167,239 A 12/1992 Cohen et al.
5,735,842 A 4/1998 Krueger et al.
(Continued)

FOREIGN PATENT DOCUMENTS

| WO | 2006127509 A2 | 11/2006 |
| WO | 2007050256 A2 | 5/2007 |
| WO | 2016081602 A1 | 5/2016 |

OTHER PUBLICATIONS

8924WO01—International Search Report for International Application No. PCT/US2018/047648.

*Primary Examiner* — Elizabeth Houston
*Assistant Examiner* — Lindsey Bachman
(74) *Attorney, Agent, or Firm* — Guy L Cumberbatch

(57) ABSTRACT

Devices and methods for securing a tissue anchor in tissue of a patient, in particular to ensure proper deployment of a cardiac tissue anchor by regulating the force or pressure of a deployment tool against the tissue. One way to ensure proper deployment force is to visualize the distal end of the tissue anchoring catheter from outside the body using a display for an imaging sensor, where the distal end of the catheter changes configuration when it is pressed against the tissue. Another method involves automatically regulating the pressure applied to the tissue prior to deployment of the tissue anchor, which may also be used in conjunction with visualization. Several safety locks to prevent deployment of the tissue anchor prior to establishment of the proper pressure are disclosed, which again may be used with visualization and/or an automated pressure regulator.

20 Claims, 20 Drawing Sheets

(51) Int. Cl.
  *A61B 17/068* (2006.01)
  *A61B 17/064* (2006.01)
  *A61B 17/00* (2006.01)
  *A61B 90/00* (2016.01)

(52) U.S. Cl.
  CPC .... *A61F 2/2427* (2013.01); *A61B 2017/0046* (2013.01); *A61B 2017/00115* (2013.01); *A61B 2017/00243* (2013.01); *A61B 2017/0409* (2013.01); *A61B 2017/0427* (2013.01); *A61B 2017/0441* (2013.01); *A61B 2017/0641* (2013.01); *A61B 2017/0649* (2013.01); *A61B 2090/3966* (2016.02); *A61F 2/2409* (2013.01); *A61F 2/2466* (2013.01); *A61F 2220/0016* (2013.01); *A61F 2230/0013* (2013.01)

(58) Field of Classification Search
  CPC ............ A61F 2002/821; A61F 2/2457; A61B 17/0401; A61B 17/068; A61B 17/0682; A61B 17/128; A61B 17/1285; A61B 2017/0409; A61B 17/3468; A61B 2017/00783; A61B 2017/0464; A61B 2017/0487; A61B 2017/0488; A61N 1/056–0575; A61N 1/0587–0595; A61N 2001/0578–0585
  See application file for complete search history.

(56) References Cited

U.S. PATENT DOCUMENTS

| | | | |
|---|---|---|---|
| 6,050,972 A | | 4/2000 | Zadno-Azizi et al. |
| 6,053,935 A | * | 4/2000 | Brenneman ........ A61B 17/0401 606/139 |
| 6,217,567 B1 | | 4/2001 | Zadno-Azizi et al. |
| 6,264,676 B1 | * | 7/2001 | Gellman ............ A61B 17/0401 600/29 |
| 6,482,228 B1 | | 11/2002 | Norred |
| 6,506,190 B1 | * | 1/2003 | Walshe ............. A61B 17/0401 606/139 |
| 6,629,534 B1 | | 10/2003 | St. Goar et al. |
| 6,764,510 B2 | | 7/2004 | Vidlund et al. |
| 6,936,052 B2 | * | 8/2005 | Gellman .......... A61B 17/00234 600/29 |
| 6,994,092 B2 | | 2/2006 | van der Burg et al. |
| 7,070,616 B2 | | 7/2006 | Majercak et al. |
| 7,077,862 B2 | | 7/2006 | Vidlund et al. |
| 7,160,322 B2 | | 1/2007 | Gabbay |
| 7,285,120 B2 | | 10/2007 | Im et al. |
| 7,320,665 B2 | | 1/2008 | Vijay |
| 7,322,957 B2 | | 1/2008 | Kletschka et al. |
| 7,404,824 B1 | | 7/2008 | Webler et al. |
| 7,556,646 B2 | | 7/2009 | Yang et al. |
| 7,678,145 B2 | | 3/2010 | Vidlund et al. |
| 7,785,366 B2 | | 8/2010 | Maurer et al. |
| 7,815,580 B2 | | 10/2010 | Viswanathan |
| 7,854,762 B2 | | 12/2010 | Speziali et al. |
| 7,901,454 B2 | | 3/2011 | Kapadia et al. |
| 7,927,370 B2 | | 4/2011 | Webler et al. |
| 7,942,928 B2 | | 5/2011 | Webler et al. |
| 8,007,428 B2 | | 8/2011 | Vijay |
| 8,070,805 B2 | | 12/2011 | Vidlund et al. |
| 8,080,808 B2 | | 12/2011 | Norris |
| 8,092,525 B2 | | 1/2012 | Eliasen et al. |
| 8,133,213 B2 | | 3/2012 | Lashinski |
| 8,216,302 B2 | | 7/2012 | Wilson et al. |
| 8,449,606 B2 | | 5/2013 | Eliasen et al. |
| 8,460,370 B2 | | 6/2013 | Zakay |
| 8,486,136 B2 | | 7/2013 | Maurer et al. |
| 8,579,967 B2 | | 11/2013 | Webler et al. |
| 8,708,885 B2 | * | 4/2014 | Khamis ............. A61B 17/0401 600/37 |
| 8,758,430 B2 | | 6/2014 | Ferrari et al. |
| 8,758,432 B2 | | 6/2014 | Solem |
| 8,778,017 B2 | | 7/2014 | Eliasen et al. |
| 8,845,717 B2 | | 9/2014 | Khairkhahan et al. |
| 8,888,843 B2 | | 11/2014 | Khairkhahan et al. |
| 8,888,844 B2 | | 11/2014 | Eliasen et al. |
| 8,932,348 B2 | | 1/2015 | Solem et al. |
| 9,119,719 B2 | | 9/2015 | Zipory et al. |
| 9,161,837 B2 | | 10/2015 | Kapadia |
| 9,232,998 B2 | | 1/2016 | Wilson et al. |
| 9,232,999 B2 | | 1/2016 | Maurer et al. |
| 9,259,317 B2 | | 2/2016 | Wilson et al. |
| 9,289,297 B2 | | 3/2016 | Wilson et al. |
| 9,474,605 B2 | | 10/2016 | Rowe et al. |
| 9,636,223 B2 | | 5/2017 | Khalil et al. |
| 2001/0010005 A1 | * | 7/2001 | Kammerer ........... A61B 17/064 606/151 |
| 2003/0050694 A1 | | 3/2003 | Yang et al. |
| 2003/0120341 A1 | | 6/2003 | Shennib et al. |
| 2003/0187494 A1 | | 10/2003 | Loaldi |
| 2004/0098081 A1 | | 5/2004 | Landreville et al. |
| 2004/0225233 A1 | | 11/2004 | Frankowski et al. |
| 2004/0267280 A1 | | 12/2004 | Nishide et al. |
| 2005/0038508 A1 | | 2/2005 | Gabbay |
| 2006/0241745 A1 | | 10/2006 | Solem |
| 2007/0093890 A1 | | 4/2007 | Eliasen et al. |
| 2007/0162071 A1 | | 7/2007 | Burkett et al. |
| 2007/0198082 A1 | | 8/2007 | Kapadia et al. |
| 2007/0219627 A1 | | 9/2007 | Chu et al. |
| 2007/0255399 A1 | | 11/2007 | Eliasen et al. |
| 2007/0265700 A1 | | 11/2007 | Eliasen et al. |
| 2007/0270943 A1 | | 11/2007 | Solem et al. |
| 2007/0282429 A1 | | 12/2007 | Hauser et al. |
| 2008/0288061 A1 | | 11/2008 | Maurer et al. |
| 2009/0048668 A1 | | 2/2009 | Wilson et al. |
| 2009/0069885 A1 | | 3/2009 | Randert et al. |
| 2009/0131880 A1 | | 5/2009 | Speziali et al. |
| 2009/0137968 A1 | | 5/2009 | Rottenberg |
| 2009/0177111 A1 | | 7/2009 | Miller et al. |
| 2009/0209910 A1 | * | 8/2009 | Kugler .................. A61B 17/11 604/103.1 |
| 2010/0022948 A1 | | 1/2010 | Wilson et al. |
| 2010/0198347 A1 | | 8/2010 | Zakay et al. |
| 2010/0298929 A1 | | 11/2010 | Thornton et al. |
| 2011/0077733 A1 | | 3/2011 | Solem |
| 2011/0184512 A1 | | 7/2011 | Webler et al. |
| 2011/0224784 A1 | | 9/2011 | Quinn |
| 2011/0264179 A1 | * | 10/2011 | Eckerdal ............. A61N 1/0573 607/116 |
| 2011/0288577 A1 | | 11/2011 | Newhauser et al. |
| 2012/0143320 A1 | | 6/2012 | Eliasen et al. |
| 2013/0325110 A1 | | 12/2013 | Khalil et al. |
| 2013/0338763 A1 | | 12/2013 | Rowe et al. |
| 2014/0309732 A1 | | 10/2014 | Solem |
| 2016/0166320 A1 | * | 6/2016 | Ciulla ................... A61B 17/22 606/14 |
| 2016/0338693 A1 | * | 11/2016 | Graul ................ A61B 17/0401 |
| 2017/0000523 A1 | | 1/2017 | Bartosch et al. |
| 2017/0196478 A1 | | 7/2017 | Hunter |
| 2017/0196509 A1 | | 7/2017 | Hunter |

\* cited by examiner

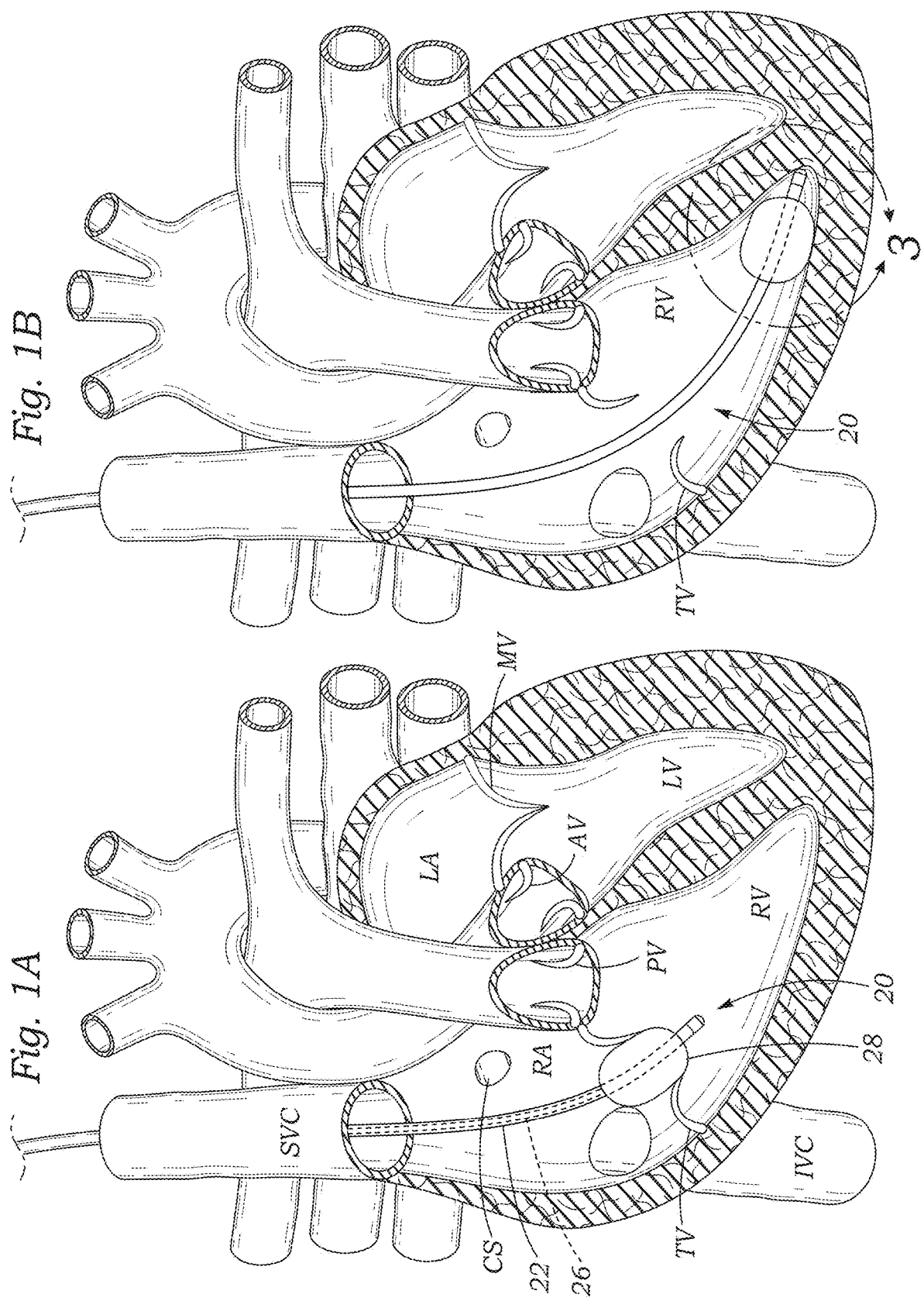

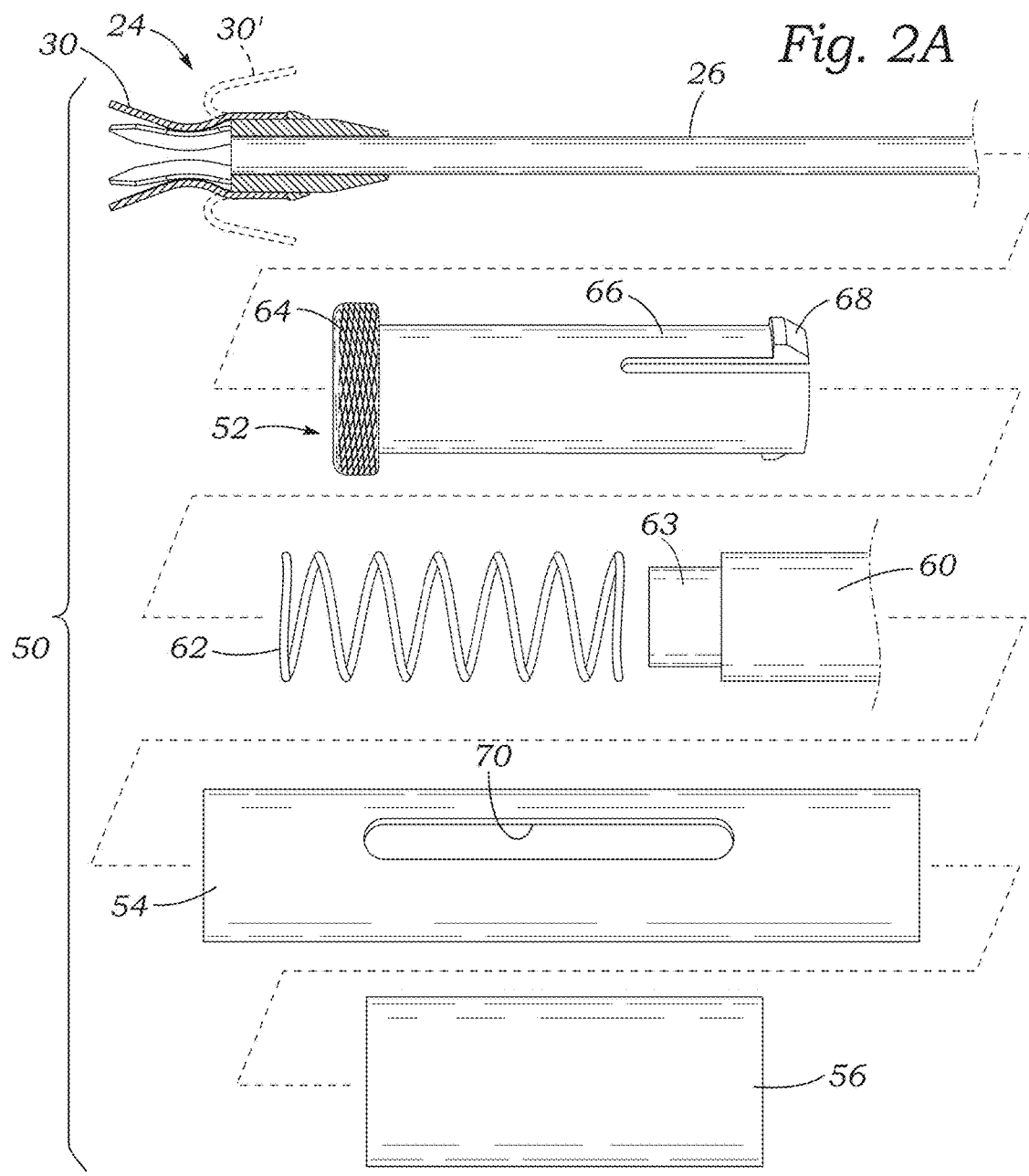
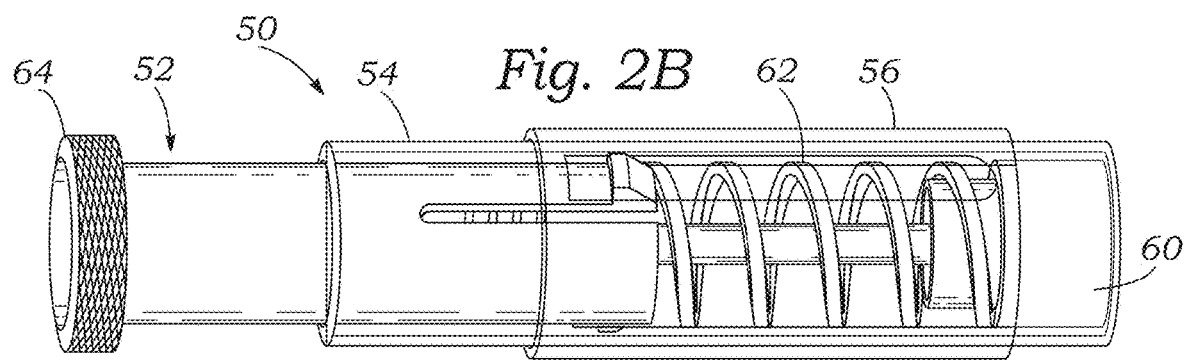

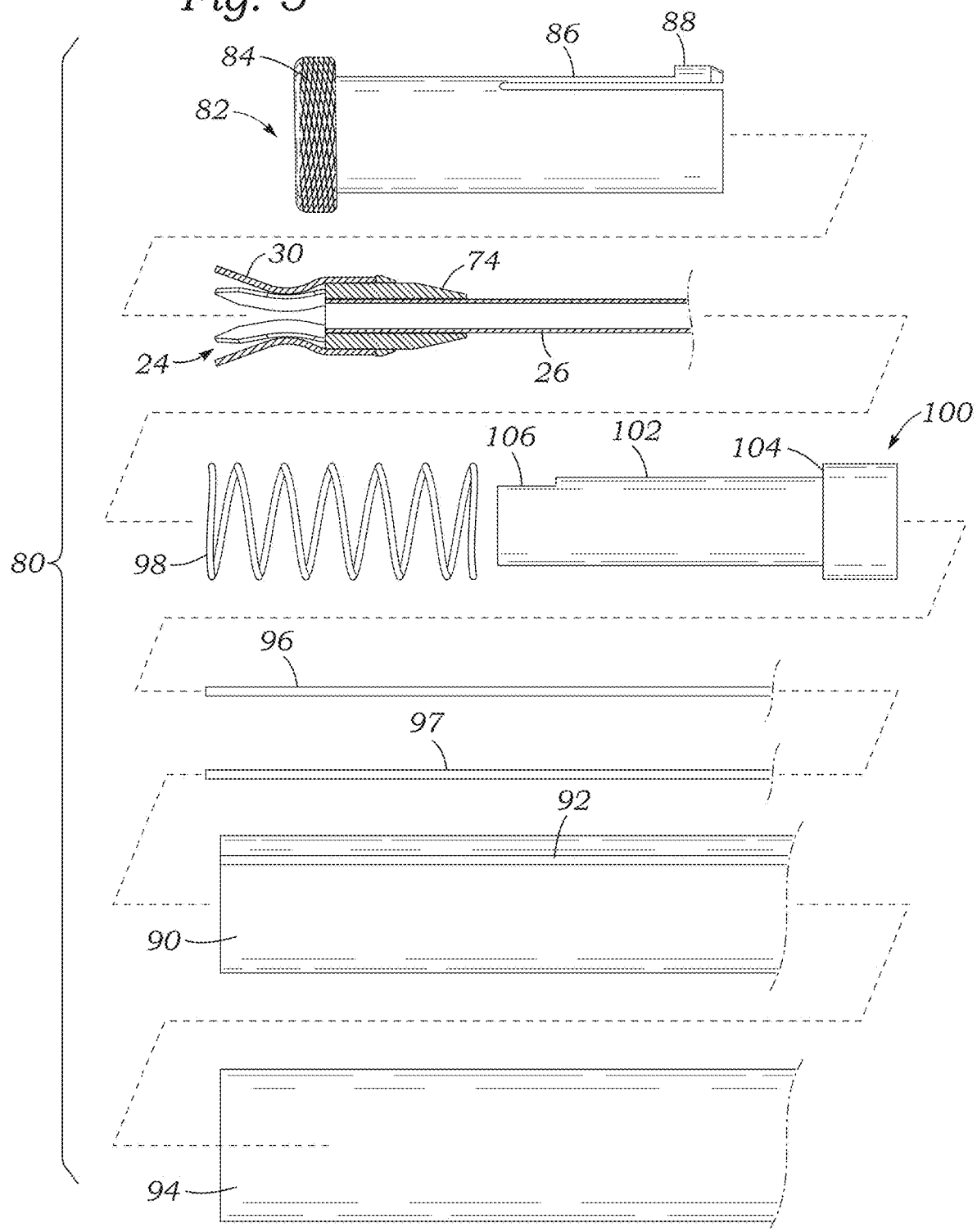

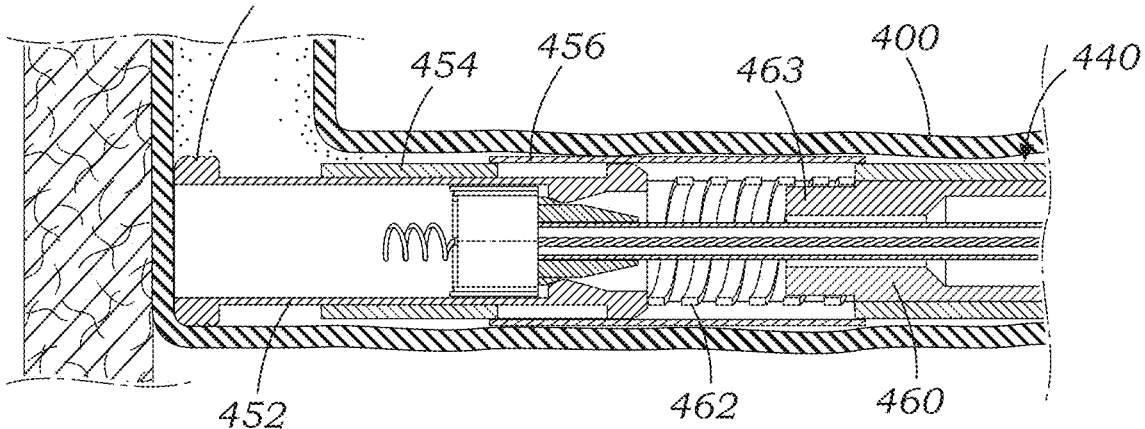
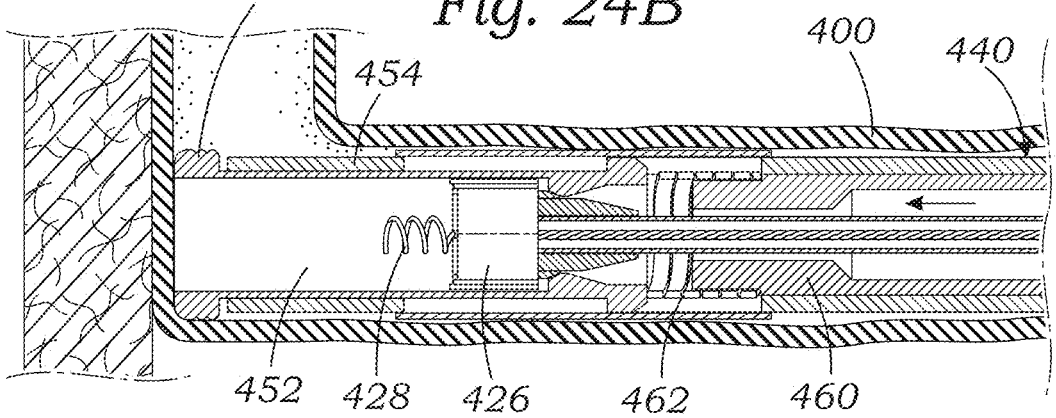
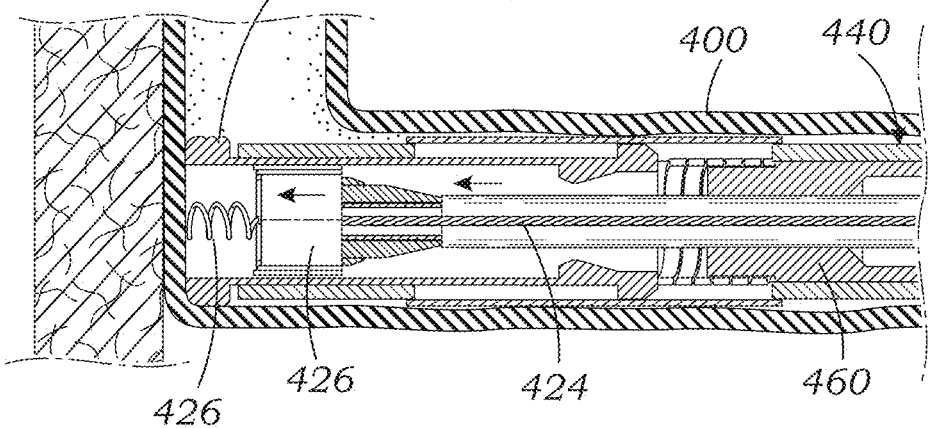

DEVICES AND METHODS FOR SECURING A TISSUE ANCHOR

RELATED APPLICATIONS

The present application claims priority to U.S. Provisional Application Ser. No. 62/550,361, filed Aug. 25, 2017, the contents of which are expressly incorporated herein by reference.

FIELD OF THE INVENTION

The present invention relates generally to devices and methods for securing a tissue anchor in tissue of a patient and, more particularly, to ensuring proper deployment of a cardiac tissue anchor by regulating the pressure of a deployment tool against the tissue.

BACKGROUND OF THE INVENTION

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

One solution is seen in U.S. Pat. No. 9,474,605 which discloses a heart valve coaptation system for reducing regurgitation through a native valve. A flexible rail having a ventricular anchor on the distal end thereof adapted to anchor into tissue within a ventricle is first deployed. A delivery catheter has a lumen through which the flexible rail passes, and a leaflet coaptation member is fixed on a distal end of the delivery catheter. Finally, a locking collet on the delivery catheter secures the axial position of the coaptation member and delivery catheter on the flexible rail. When in place, the coaptation member reduces or eliminates regurgitation through the native valve, in particular a tricuspid heart valve.

In order for systems similar to those disclosed in U.S. Pat. No. 9,474,605 to properly function, the initial deployment of the flexible rail is important, a lot of which depends on the location and secure deployment of the tissue anchor. There is a need for more reliable anchoring techniques.

SUMMARY OF THE INVENTION

The present invention relates generally to devices and methods for securing a tissue anchor in tissue of a patient, in particular to ensure proper deployment of a cardiac tissue anchor by regulating the force or pressure of a deployment tool against the tissue. One way to ensure proper deployment force is to visualize the distal end of the tissue anchoring catheter from outside the body using a display for an imaging sensor, where the distal end of the catheter changes configuration when it is pressed against the tissue. Another method involves automatically regulating the pressure applied to the tissue prior to deployment of the tissue anchor, which may also be used in conjunction with visualization. Several safety locks to prevent deployment of the tissue anchor prior to establishment of the proper pressure are disclosed, which again may be used with visualization and/or an automated pressure regulator.

System with Visibility Indicators

In one aspect, a system for ensuring secure anchoring of a tissue anchor within tissue in a patient's body using external visualization is disclosed. The system has a tissue anchor deployment system including a proximal handle connected to an elongated flexible tube having a lumen within which translates an elongated tissue anchor tool with a distal tissue anchor thereon suitable for piercing and anchoring into tissue. A tissue contact indicator assembly configured to be visible from outside the body on a display for an imaging sensor is located adjacent a distal end of the flexible tube. The assembly has a movable member that in a first position presents a first visual image on the display for the imaging sensor prior to contact between the distal end of the flexible tube and tissue, and presents a second visual image distinct from the first visual image after moving to a second position when a predetermined pressure is applied between the distal end of the flexible tube and the tissue. The predetermined pressure is calibrated to ensure that the tissue anchor securely embeds into the tissue when the tissue anchor tool is subsequently advanced.

The movable member of the external visualization system may comprise a distal tubular housing having a relatively thin-walled body and a distal ring that is thicker than the thin-walled body and consequently more visible to the imaging sensor. The tubular housing is arranged to slide proximally within the flexible tube, and the flexible tube has a tubular housing frame at a distal end with a relatively thick wall that is visible to the imaging sensor, wherein proximal movement of the distal tubular housing causes the distal ring to move into proximity with the tubular housing frame and form the second visual image. In one embodiment, the distal ring exhibits at least one chamfer or an outer surface that is uneven for greater visibility to the imaging sensor. Preferably, a spring is positioned between the tubular housing and the flexible tube which determines the predetermined pressure. In addition, a tensioner may be positioned intermediate the tissue contact indicator assembly and the proximal handle which exerts a proximal force on the elongated tissue anchor tool, the tissue anchor having a size that interferes with a portion of the tubular housing so as to retract the tubular housing within the flexible tube.

Alternatively in the external visualization system, the movable member may comprise a distal tubular housing having a first radiopaque band thereon that is more visible to the imaging sensor than a remainder of the tubular housing. The tubular housing is then arranged to slide proximally within the flexible tube and the flexible tube has a second radiopaque band thereon. The first visual image thus shows the first and second radiopaque bands spaced a first distance apart and the second visual image shows the first and second radiopaque bands closer together than the first distance.

The external visualization system may further include a locking member that prevents movement of the movable member and is manually disengaged using an actuator on the proximal handle. Also, the elongated tissue anchor tool may comprise a flexible rail affixed to the tissue anchor or is detachable from the tissue anchor. Desirably, the tissue anchor is selected from the group consisting of a plurality of distally-directed sharp tines having an outward elastic bias such that they curl outward upon release from a surrounding constraint, and a corkscrew-like tine.

Ready to File System

Another system disclosed herein for ensuring secure anchoring of a tissue anchor within tissue in a patient's body comprises a tissue anchor deployment system including a proximal handle connected to an elongated flexible tube having a lumen within which translates an elongated tissue anchor tool with a distal tissue anchor thereon suitable for piercing and anchoring into tissue. A tissue contact pressure regulator assembly adjacent a distal end of the flexible tube has a pusher shaft that is in a first position prior to contact between the distal end of the flexible tube and tissue and is coupled to move with the tissue anchor tool. The tissue contact pressure regulator assembly includes a spring positioned between the pusher shaft and the distal end of the flexible tube, such that after contact of the distal end of the flexible tube with tissue, initial advancement of the pusher shaft to a second position displaces the tissue anchor tool to the distal end of the flexible tube and compresses the spring to apply a predetermined pressure between the distal end of the flexible tube and the tissue. Further advancement of the tissue anchor tool embeds the tissue anchor into the tissue, wherein the predetermined pressure is calibrated to ensure that the tissue anchor securely embeds into the tissue when the tissue anchor tool is advanced.

In the ready-to-fire system, the spring may be fully compressed when the pusher shaft is in the second position and remains stationary during further advancement of the tissue anchor tool. The distal end of the flexible tube may comprise a distal tubular housing having a relatively thin-walled body and a distal ring that is thicker than the thin-walled body and consequently more visible to the imaging sensor. The tubular housing is arranged to slide proximally within the flexible tube, and the flexible tube has a tubular housing frame at a distal end with a relatively thick wall that is visible to the imaging sensor. Proximal movement of the distal tubular housing thus causes the distal ring to move into proximity with the tubular housing frame which is visible from outside the body on a display for an imaging sensor. The system may further include a tensioner positioned intermediate the tissue contact pressure regulator assembly and the proximal handle which exerts a proximal force on the elongated tissue anchor tool, the tissue anchor having a size that interferes with a portion of the tubular housing so as to retract the tubular housing within the flexible tube.

The ready-to-fire system may further include a locking member that prevents movement of the tubular housing and is manually disengaged using an actuator on the proximal handle. Also, the elongated tissue anchor tool may comprise a flexible rail affixed to the tissue anchor or is detachable from the tissue anchor. Desirably, the tissue anchor is selected from the group consisting of a plurality of distally-directed sharp tines having an outward elastic bias such that they curl outward upon release from a surrounding constraint, and a corkscrew-like tine.

In the ready-to-fire system the spring may be a coil spring positioned around a narrow distal end of the pusher shaft that engages the flexible tube and compresses as the narrow distal portion passes through the flexible tube.

In any of the systems described herein, a guide balloon may be positioned around the distal end of the flexible tube that helps prevent entanglement of the distal end of the flexible tube with anatomical structures.

Removable Lock

A third system for ensuring secure anchoring of a tissue anchor within tissue in a patient's body comprises a tissue anchor deployment system including a proximal handle connected to an elongated flexible tube having a lumen within which translates an elongated tissue anchor tool with a distal tissue anchor thereon suitable for piercing and anchoring into tissue. A tissue contact pressure regulator assembly adjacent a distal end of the flexible tube has a locking member that has a first position that prevents advancement of the tissue anchor tool and is displaceable to a second position that permits advancement of the tissue anchor tool. When the distal end of the flexible tube is pressed against tissue, the pressure regulator assembly applies a predetermined pressure between the distal end of the flexible tube and the tissue. The predetermined pressure is calibrated to ensure that the tissue anchor securely embeds into the tissue when the locking member is displaced to the second position and the tissue anchor tool is advanced into the tissue.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIGS. 1A and 1B are cutaway views of the human heart in a systolic phase showing introduction of an anchoring catheter into the right ventricle as a first step in deploying a device for reducing tricuspid valve regurgitation;

FIG. 2A is an exploded view of a tissue anchor (shown partly in section) along with an assembly of components on the distal end of the anchoring catheter for regulating the pressure of the catheter against tissue including an internal spring member, and FIG. 2B is an assembled view of the pressure regulating assembly;

FIG. 5 is an exploded view of an alternative pressure regulating assembly of components for use on the distal end of a tissue anchoring catheter also having an internal spring and calibrated so that deployment of the tissue anchor is semi-automated;

FIGS. 24A-24C are sectional views of steps in utilizing an exemplary tissue anchoring catheter through the sleeve-like annuloplasty ring to install one of the anchors.

DETAILED DESCRIPTION OF THE PREFERRED EMBODIMENTS

Figure 1C:
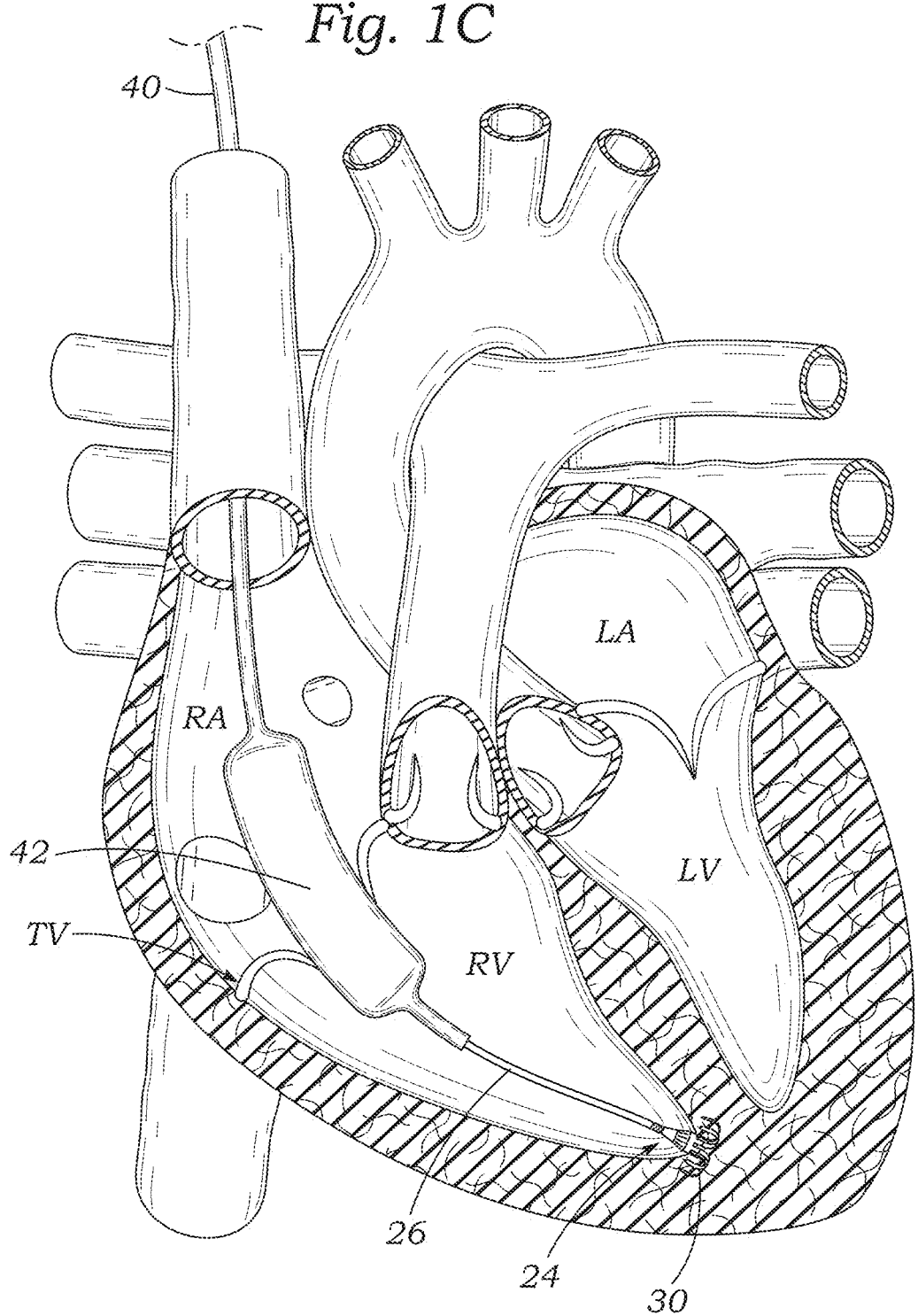
FIG. 1C is a cutaway view of the human heart after securing a tissue anchor in the right ventricle and then advancing a device for reducing valve regurgitation into position within the tricuspid annulus over an elongated tissue anchor rail.

The following description refers to the accompanying drawings, which illustrate specific embodiments of the invention. Other embodiments having different structures and operation do not depart from the scope of the present invention.

Various embodiments of the present disclosure are directed to devices and methods for ensuring accurate placement and secure deployment of a tissue anchor, in particular for a tissue anchor embedded in an internal wall of the heart. For instance, U.S. Pat. No. 9,474,605 (expressly incorporated herein) discloses systems that require anchoring devices within the wall of the left or right ventricle. Visualization such as via fluoroscopy helps with locating the tissue anchor within the ventricle, but by itself cannot inform the operator whether the tissue anchor has contacted the internal ventricular surface with sufficient force. Tissue anchors that embed themselves within tissue may not penetrate far enough into the tissue if the deployment catheter is not pushed against the target tissue with adequate force. Conversely, excessive force may cause damage to the tissue surface or even cause an unwanted puncture through a tissue wall. The same problems anchoring devices within the heart ventricles arise for tissue anchors deployed in other internal body cavities, and the present application should not be considered limited to cardiac tissue anchors. To explain the solutions disclosed herein in the context of cardiac tissue anchors, an understanding of the internal anatomical structures of the heart is provided first.

FIGS. 1A and 1B are cutaway views of the human heart in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery (also not identified). Each of these valves has flexible tissue leaflets extending inward across the respective orifices that come together or "coapt" in the flowstream to form the one-way fluid occluding surfaces. The regurgitation reduction devices of the present application are primarily intended for use to treat the atrioventricular valves, and in particular the tricuspid valve. Therefore, anatomical structures of the right atrium RA and right ventricle RV will be explained in greater detail, though it should be understood that the devices described herein may equally be used to treat the mitral valve MV with an anchor placed in the left ventricle LV.

The right atrium RA receives deoxygenated blood from the venous system through the superior vena cava SVC and the inferior vena cava IVC, the former entering the right atrium above, and the latter from below. The coronary sinus CS is a collection of veins joined together to form a large vessel that collects deoxygenated blood from the heart muscle (myocardium), and delivers it to the right atrium RA. During the diastolic phase, or diastole, the venous blood that collects in the right atrium RA is pulled through the tricuspid valve TV by expansion of the right ventricle RV. In the systolic phase, or systole, seen in FIGS. 1A and 1B, the right ventricle RV collapses to force the venous blood through the pulmonary valve PV and pulmonary artery into the lungs. During systole, the leaflets of the tricuspid valve TV close to prevent the venous blood from regurgitating back into the right atrium RA. It is during systole that regurgitation through the tricuspid valve TV becomes an issue, and the devices of the present application are beneficial.

FIGS. 1A and 1B show introduction of a tissue anchoring catheter 20 into the right ventricle as a first step in deploying a device of the present application for reducing tricuspid valve regurgitation. The catheter 20 includes an outer sheath 22 defining an internal lumen through which pass a tissue anchor 24 (see FIG. 1C) and anchor rail 26. The anchoring catheter 20 enters the right atrium RA from the superior vena cava SVC after having been introduced to the subclavian vein using well-known methods, such as the Seldinger technique. A guide balloon 28 adjacent the distal end of the catheter 20 assists passage through the leaflets of the tricuspid valve TV and helps reduce the occurrence of chordal entanglement. The balloon is inflated in the right atrium RA and is then deflated once the anchoring catheter 20 has reached the right ventricle. The physician advances the anchoring catheter 20 until its distal tip is touching the target anchoring site within the right ventricle, as seen in FIG. 1B.

FIG. 1C shows the tissue anchor rail 26 after installing the tissue anchor 24 at the apex of the right ventricle RV. The tissue anchor 24 and anchor rail 26 were expelled distally from within the catheter sheath 22, and the tissue anchoring catheter 20 has desirably been removed completely from the patient's body in favor of a second catheter 40. Preferably, the catheter 40 has a central lumen and advances over the anchor rail 26. The operator positions a spacer or coapting member 42 mounted on the second catheter 40 within the leaflets of the tricuspid valve TV. Various configurations of coapting members 42 are known in the art, in particular as disclosed in U.S. Pat. No. 9,474,605. The second catheter 40 is desirably locked in position on the anchor rail 26 such that the coapting member 42 remains between the tricuspid valve leaflets. The presence of a coapting member 42 is intended to fill any gaps between the tricuspid valve leaflets which might result in regurgitation, and thus function something like a plug between the leaflets.

The exemplary tissue anchor 24 includes a plurality of circumferentially distributed and distally-directed sharp tines or barbs 30 that pierce the tissue of the ventricular apex. The barbs 30 are held in a stressed configuration within the sheath 22, and are provided with an outward elastic bias so that they curl outward upon release from the sheath. Desirably the barbs 30 are made of a super-elastic metal such as Nitinol. The outward curling of the barbs 30 is caused by the elastic material reverting to its relaxed configuration, the barbs 30 being previously held in a stressed elongated configuration within the catheter sheath 22. The operation to embed the tissue anchor 24 may be controlled under visualization, such as by providing radiopaque markers in and around the tissue anchor 24 and distal end of the catheter sheath 22, as will be explained.

The exemplary tissue anchor 24 is disclosed in U.S. Pat. No. 9,474,605, expressly incorporated herein, which also discloses other tissue anchors that may also benefit from the solutions described herein. U.S. Pat. No. 8,932,348, also expressly incorporated herein, provides further details of tissue anchors similar to the tissue anchor 24. Tissue anchors that include tines or barbs that pierce the tissue and elastically change shape to hold onto the tissue especially benefit from the concepts disclosed herein. However, other tissue anchors that require a minimum amount of contact force in order to properly deploy may also be modified to include the various embodiments disclosed herein. Applicants therefore emphasize that unless any particular claim enumerated below specifies the type of tissue anchor, all such "piercing" tissue anchors are suitable candidates.

To facilitate central positioning of the anchor rail 26 during deployment the device is implanted with the assistance of an imaging sensor such as an ex vivo (outside the body) fluoroscope. For example, after properly positioning the patient so as to maximize the view of the target annulus, e.g., the tricuspid annulus, a pigtail catheter is placed in the right ventricle and contrast injected. This allows the user to see a clear outline of the annulus and the right ventricle. At this point, a frame of interest is selected (e.g., end systole) in which the annulus is clearly visible and the annulus to ventricular apex distance is minimized. On the monitor, the outline of the right ventricle, the annulus, and the pulmonary artery are traced. The center of the annulus is then identified and a reference line placed 90° thereto is drawn extending to the right ventricular wall. This provides a clear linear target for anchoring. In a preferred embodiment, the anchor 24 is preferably located in the base of the ventricle between the septum and the free wall.

Aligning the anchor rail 26 in this manner helps center the eventual positioning of a coapting element of the system within the tricuspid leaflets. If the coapting element is offset to the anterior or posterior side, it may get stuck in the tricuspid valve commissures resulting in leakage in the center of the valve. An alternative method is to place a device such as a Swan Ganz catheter through the right ventricle and into the pulmonary artery to verify that the viewing plane is parallel to the anterior/posterior viewing plane. Addition of a septal/lateral view on the fluoroscope may be important to center the anchor in patients that have a dilated annulus and right ventricle. Further, the presence of the guide balloon 28 (FIG. 1A) centers the anchoring catheter 20 through the leaflets of the tricuspid valve TV and reduces large misalignments.

Various imaging sensors may be utilized to visualize the position and configuration of the tissue anchoring catheter 20 and surrounding anatomical structures. Fluoroscopy is essentially a continuous X-ray beam that can distinguish between various anatomical structures and surgical instruments or materials within the body. Alternatives to fluoroscopy include ultrasound, optical imaging, magnetic resonance imaging (MRI), and the like. Some of these devices function exclusively from outside the body (ex vivo), while others may require an in vivo probe. All have some type of display (e.g., video screen) that informs the operator about the position and configuration of various objects in the field of visualization. The term imaging sensor refers to the sensing transducer for any of these technologies and should not be considered limited to fluoroscopy, even though that is most commonly used during cardiac surgery.

The present application contemplates several methods for ensuring that the proper pressure is applied by the tissue anchoring catheter against the tissue so the tissue anchor securely deploys. One method involves visualizing the distal end of the tissue anchoring catheter from outside the body using a display for an imaging sensor, where the distal end of the catheter changes configuration when it is pressed against the tissue. Another method involves automatically regulating the pressure applied to the tissue prior to deployment of the tissue anchor, which may also be used in conjunction with visualization. Several safety locks to prevent deployment of the tissue anchor prior to establishment of the proper pressure are disclosed, which again may be used with visualization and/or an automated pressure regulator. Indeed, a number of separate technical aspects disclosed herein may be combined in various ways, and the application should not be considered limited to any one particular illustrated embodiment. More specifically, it should be understood that any illustrated embodiment shown and described herein can be combined with any other illustrated embodiment as long as the technical aspects are not mutually exclusive or otherwise physically redundant.

Most notably, the pressure-regulating aspects of the devices and methods for ensuring accurate placement and secure deployment of a tissue anchor such as anchor 24 shown in FIGS. 1A-1C are suitable for use with an anchor by itself. That is, the techniques may be used to embed an anchor 24 without connection to a tether such as the anchor rail 26. Indeed, one embodiment for deploying tissue anchors by themselves is described below with reference to FIGS. 21-24. Accordingly, any and all of the subsequently described devices and methods may be combined in a system similar to that shown in FIGS. 21-24 that deploys tissue anchors by themselves, absent a tether.

Visualization of the Tip of the Tissue Anchoring Catheter

A first technique to ensure proper pressure is applied by the catheter against the tissue involves visualization by an imaging sensor. FIG. 2A is an exploded view of a tissue anchor 24 (shown partly in section) and rail 26 along with an assembly of components 50 on the distal end of the anchoring catheter 20 for regulating the pressure of the catheter against tissue including an internal spring member, and FIG. 2B is an assembled view of the pressure regulating assembly 50. It should be noted that the tines 30 of the tissue anchor 24 are shown flexed into elongated shapes for passage through the anchoring catheter 24, and also shown in dashed line 30' in their relaxed configuration curled back upon themselves which occurs upon ejection from the catheter and deployment into tissue. Also, the anchor rail 26 is cut short for clarity, and may be many feet long. The assembly 50 includes a distal tubular housing 52 that slides axially within a tubular housing frame 54 that is surrounded by a thin tubular cover 56. A distal end of an elongated pusher 60 engages via a coil spring 62 a proximal end of the housing frame 54. The coil spring 62 is centered on a short radially recessed portion 63 of the pusher 60 and extends between the pusher and a proximal end of the tubular housing 52. The distal end of the pusher 60 may be fixed with respect to the housing frame 54, as well as to the proximal end of the coil spring 62.

The tubular housing 52 includes an enlarged distal tip 64 formed as a thick echogenic ring, such as by providing changes in diameter, chamfers or knurling on an exterior periphery thereof, as shown. (In this context, "echogenic" does not strictly refer to the sound reflective properties of the distal tip 64, but to its ability to effectively reflect various types of waves, such as the X-rays used in fluoroscopy.) The tip 64 preferably has a chamfered front outer corner which also aids in preventing tissue from getting caught on the tip. The majority of the tubular housing 52 has a much thinner wall thickness than the relatively large mass distal tip 64 and terminates at its proximal end in a plurality of axial slots that form a pair of diametrically-opposed cantilevered sections 66 each having an outwardly-directed retention tab 68. The exterior diameter of the proximal end of the tubular housing 52 fits closely within the lumen of the housing frame 54, and each retention tab 68 has a proximal ramp that permits the cantilevered sections 66 to flex inward upon insertion of the tubular housing 52 into the distal end of the housing frame 54. Rotational alignment of the tubular housing 52 within the housing frame 54 enables the retention tabs 68 to snap outward into axial slots 70.

As seen in FIG. 2B, the tubular cover 56 may be adhered or welded to the outside of housing frame 54 and conceals the slots 70. Because the distal end of each of the retention tabs 68 has a radial face, the tubular housing 52 is retained within the housing frame 54 and can slide axially therein between distal and proximal positions.

FIGS. 3A-3D are sectional views of steps in positioning the exemplary tissue anchoring catheter having the distal assembly 50 of components over a target tissue site T. It should be noted that for clarity these figures do not show an outer flex shaft or sheath such as shown at 22 in FIG. 1A (e.g., Pebax material) that surrounds the assembly 50, nor the guide balloon 28 mentioned above which would be incorporated into the outer shaft.

In use, the operator negotiates the catheter 20 through the body into proximity to the tissue target T, as explained above in the context of deploying a cardiac anchor. The coil spring 62 biases the distal tubular housing 52 distally so that the distal tip 64 projects from within the housing frame 54. Engagement of the tabs 68 on the tubular housing 52 with the distal extent of the axial slots 70 in the housing frame 54 retains the housing within the frame. It will be understood, however, that the tubular housing 52 may be displaced proximally into the housing frame 54 against the spring 62, at least to the compressive limit of the spring or when the housing contacts some other physical impediment.

Figure 3A:
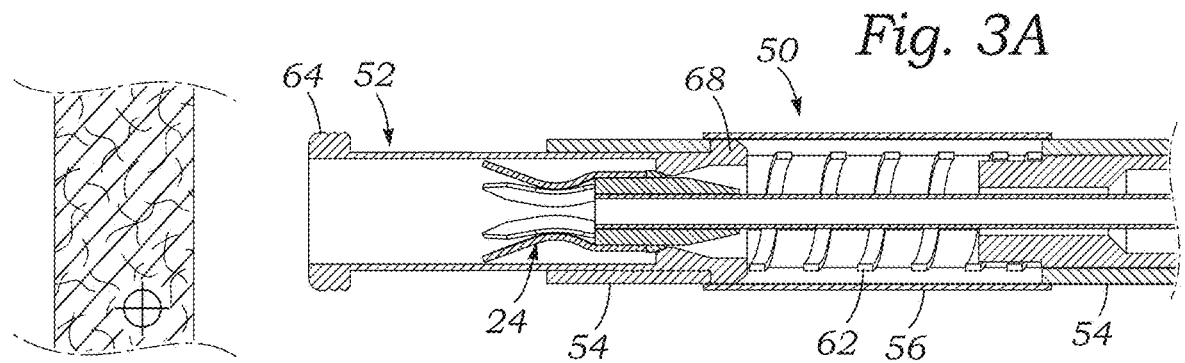
FIGS. 3A-3D are sectional views of steps in positioning an exemplary tissue anchoring catheter over a target tissue site.
Figure 3B:
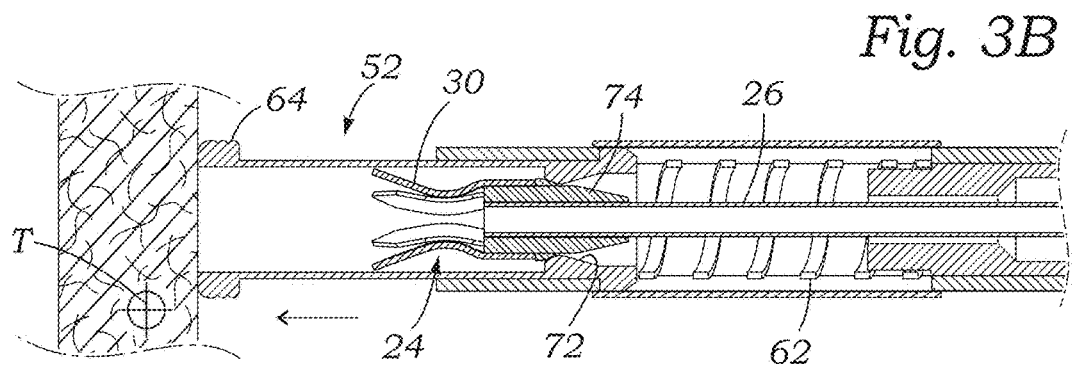

FIG. 3B illustrates the distal advancement of the entire distal catheter assembly 50 until the distal tip 64 contacts the tissue surface tissue surface. As mentioned above, this position of the catheter prior to deployment of the tissue anchor 24 is typically accomplished under visualization.

FIG. 3B also illustrates an internal annular ridge 72 formed on a proximal end of the tubular housing 52. The ridge 72 interferes with a tapered hub 74 that forms a part of the tissue anchor 24. In particular, the hub 74 fastens around the anchor rail 26 and the tines 30 are secured to the hub. The interference between the inner ridge 72 and tissue anchor hub 74 provides a stop that prevents the tissue anchor 24 from being pulled out of the tubular housing 52 and into the middle of the spring 62. Engagement between the ridge 72 and hub 74 is another impediment prevents the moving housing 72 from ever becoming detached completely from the catheter, as it is always retained thereon by the tissue anchor 24.

Figure 3C:
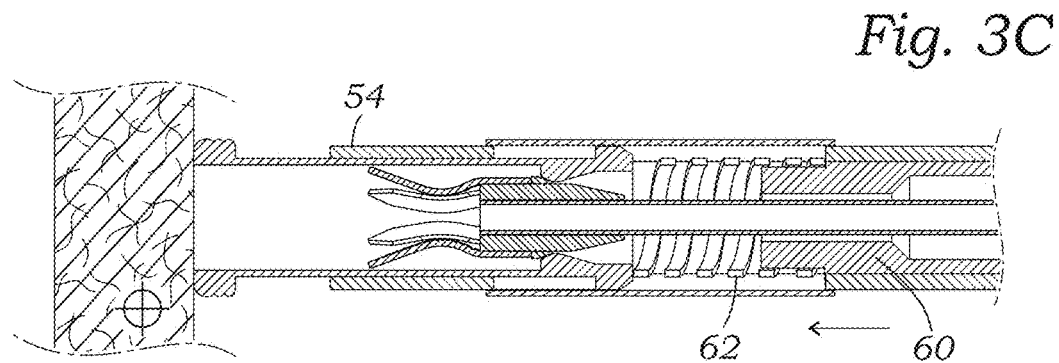
Figure 3D:
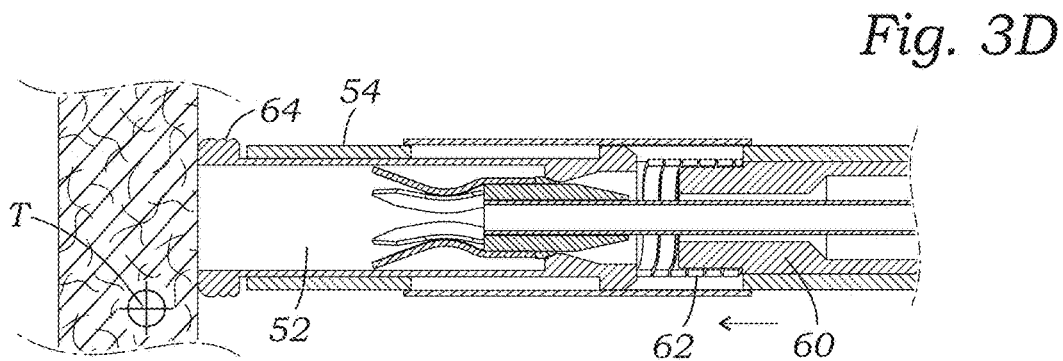

Once in the position of FIG. 3B, the operator determines whether the distal tip 64 is centered over the tissue target T. In the meantime, the operator may further advance the catheter 50 and connected housing frame 54 to compress the spring 62, as seen in FIGS. 3C and 3D. Although not shown, the pusher 60 preferably extends back to a proximal handle and an actuator which slides it forward and backwards, or is coupled to a secondary shaft (not shown) which extends proximally to the handle. It should be understood that there are various ways for axially displacing the pusher 60. At the point where the spring 62 is fully compressed (or least compressed to a desired amount), a distal portion of the housing frame 54 comes into close proximity with the thick distal tip 64 of the tubular housing 52. It should be noted that the thicker distal tip 64 is less traumatic to tissue against which it is pressed.

Figure 10A:
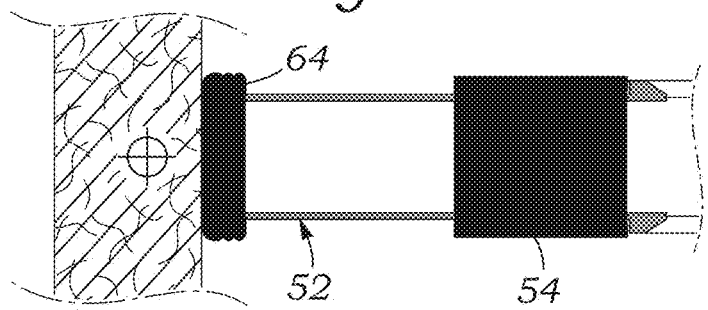
FIGS. 10A-10B are schematic views of the distal end of a tissue anchoring catheter of the present application showing different fluoroscopic images visible using an external imaging sensor of two positions of the pressure regulating assembly.
Figure 10B:
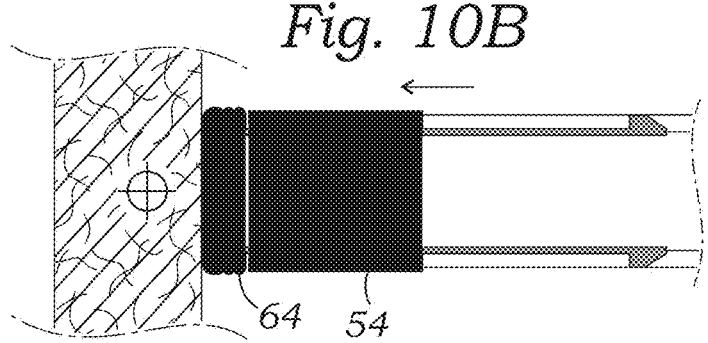

A schematic image of the appearance of the distal assembly of components 50 in this sequence is seen in FIGS. 10A and 10B, wherein the relatively thick housing frame 54 shows up as a dark rectangular mass that eventually moves into close proximity with the relatively large mass distal tip 64 that also shows up as dark on the image display. The remainder of the tubular components have lesser wall thicknesses, and in contrast show up less distinctly on the image display. The operator can thus tell when the spring 62 has been fully compressed (or least compressed to the requisite amount). However, upon further examination of the image display from the position of the components relative to the anatomy in FIG. 3D, the operator may conclude that the catheter is not centered over the tissue target T, and thus will not deploy the tissue anchor 24.

Figure 4A:
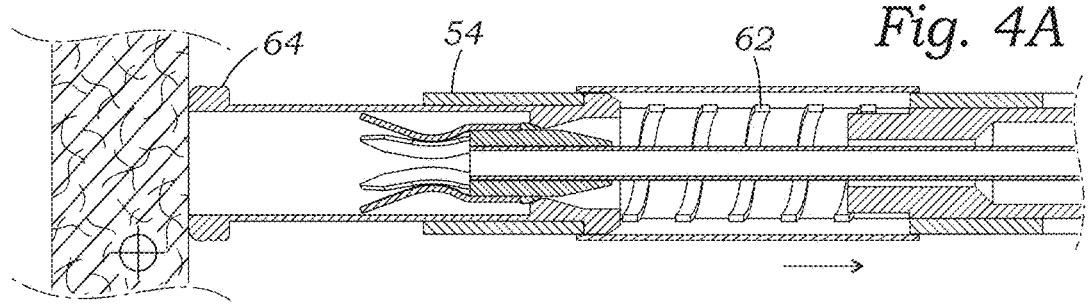
FIGS. 4A-4E are sectional views of steps of repositioning the tissue anchoring catheter and then deploying the tissue anchor into the tissue using the pressure regulating assembly.
Figure 4B:
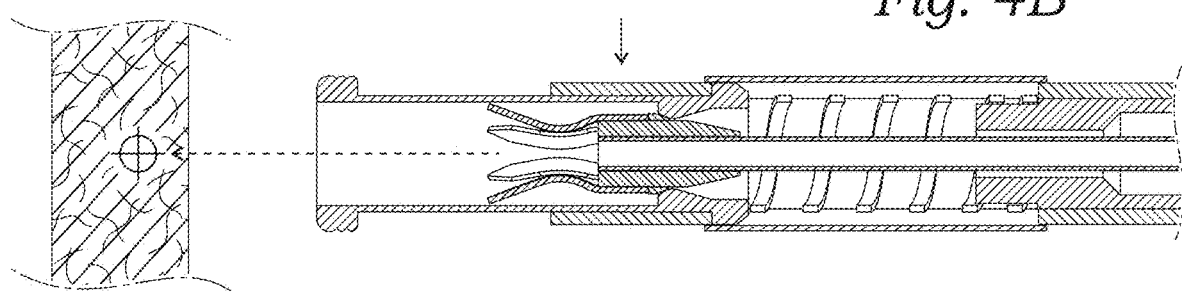
Figure 4C:
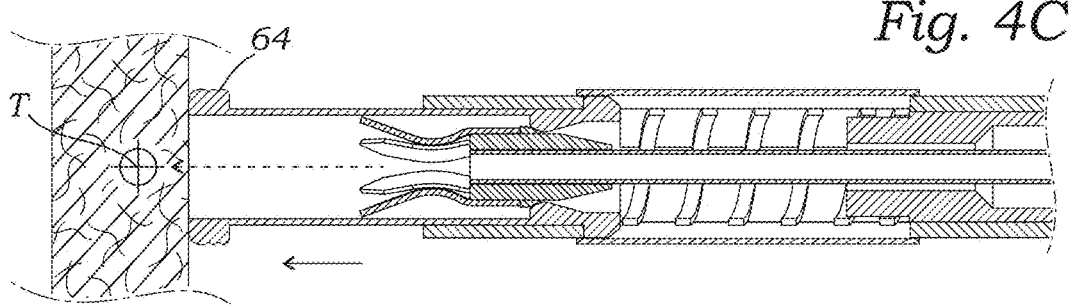

FIG. 4A illustrates a step of repositioning the tissue anchoring catheter by first retracted proximally the pusher 60 and housing frame 54. This relaxes the spring 62 and separates the distal end of the housing frame 54 from the distal ring 64. FIG. 4B shows lateral displacement of the catheter until it is centered over the tissue target T, at which point it is once again advanced until the distal tip 64 is in contact with the tissue wall, as in FIG. 4C. Subsequently, the catheter pusher 60 is once again displaced distally to advance the housing frame 54 relative to the tubular housing 52.

Figure 4D:
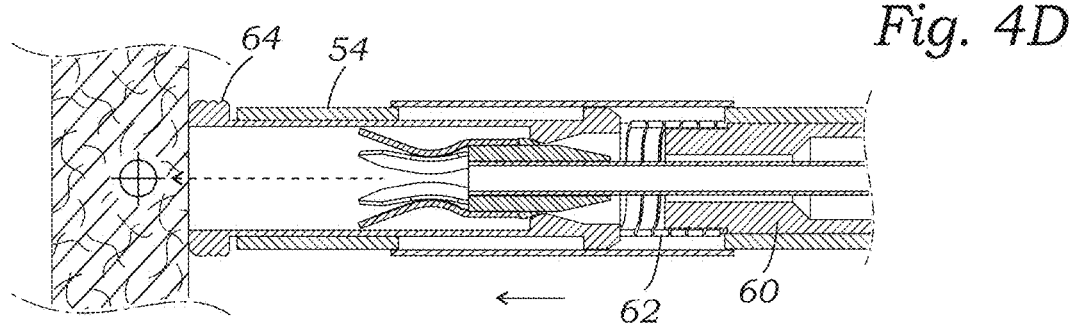

In FIG. 4D, the thick distal end of the housing frame 54 has once again reached the echogenic distal tip 64, which convergence shows up clearly on the external imaging display (see, e.g., FIG. 10B) thus notifying the operator that the desired compressive force for anchor deployment has been reached. Several alternative configurations of a distal assembly of components on the catheter which affords good visibility using an imaging sensor/display are disclosed herein, some of which are discussed below with regards to FIGS. 11 and 12.

As mentioned above, the coil spring 62 may be completely compressed, as shown, though this is not strictly necessary and the spring may be only partly compressed. In either case, compression of the spring 62 at the moment when the distal end of the housing frame 54 reaches the distal tip 64 provides a calibrated and desirable compressive force of the catheter against the tissue. That is, the spring constant is calibrated so that linear compression to the extent seen in FIG. 4D produces a contact force which will ensure that the tissue anchor 24 will properly embed within the tissue once advanced from the tubular housing 52. As will be understood, the particular contact force for which the spring 62 is calibrated depends on a number of factors such as the size and configuration of the tissue anchor 24, the character of the tissue into which anchor is embedded, and the subsequent forces expected to be imparted to the anchor rail 26 once fully implanted, among others. In an exemplary embodiment, the illustrated tissue anchor 24 is properly anchored within the ventricular tissue when expelled from the catheter that exerts a contact force against the tissue of between 0.5-2.0 N, and more preferably about 1.0 N.

Figure 4E:
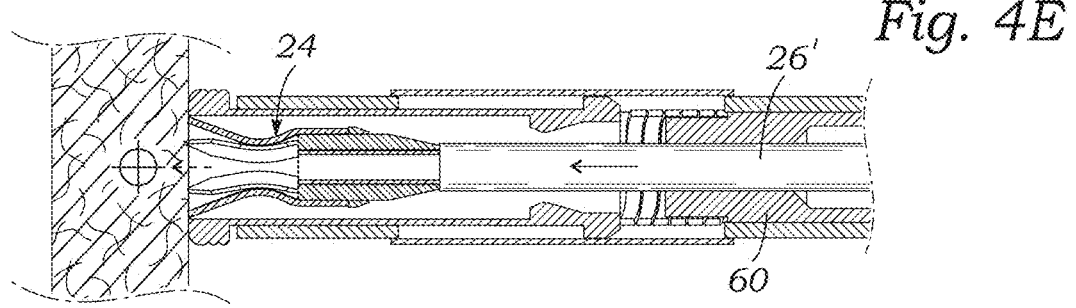

Subsequently, as seen in FIG. 4E, the operator separately advances the anchor rail 26 through a lumen in the pusher 60. Although not shown, further advancement of the tissue anchor 24 causes it to be embedded within the tissue. Because of the compressive force imparted by the catheter 20 on the tissue, an equal and opposite reactive force from the tissue is established. The tissue anchor 24 encounters this force upon emerging from the distal tip 64, and consequently deploys in the expected manner.

It should be noted that the "anchor rail 26" is shown as a hollow flexible tube, but may be a braided cable to the end of which attaches the tissue anchor 24. In that case, a thin-walled tubular pusher may be used over the cable that engages the tissue anchor 24. A tubular pusher 26' is actually shown in FIG. 4E. It should also be noted that the anchor rail 26 has sufficient linear compressive strength to advance the tissue anchor 24, and thus functions as a pusher in itself. In this regard, the anchor rail 26 acts as an anchor tool to advance the tissue anchor 24. As mentioned above, the anchor 24 may be installed by itself without the anchor rail 26, such as for instance if the two components are detachable, in which case the anchor rail 26 functions simply as a pusher tool and not as a subsequent tether for the anchor 24.

Automated Deployment of the Tissue Anchor and Deployment Locks

The tissue anchor catheter 20 described above requires advancement of a portion of the catheter to establish a proper compressive force against the target tissue followed by a separate or autonomous advancement of the tissue anchor rail. However, these functions may be combined into a single movement. That is, the same element that creates the compressive force may also advance the tissue anchor in a so-called "push-to-fire" configuration. As will be seen, this configuration of tissue anchor catheter may be utilized with or without simultaneous visualization of the distal tip. That is, if the compressive force is actuated automatically by advancing the catheter into the tissue wall, there may be no need to ensure proper force regulation by external imaging. On the other hand, adding visualization provides redundancy in the system, and as will be explained below, may actually be necessary for proper operation.

FIG. 5 illustrates an exploded assembly of components 80 for a distal end of a tissue anchor catheter that combines the force generation function with the tissue anchor advancement function in one action. The assembly 80 includes a distal tubular housing 82 again having a ring 84 on a distal end with a wide echogenic outer surface and chamfered forward corner that contacts the tissue wall. The proximal portion of the tubular housing 82 has a thin wall for fluoroscopic contrast with the ring 84, and features a pair of longitudinal slits that create at least one cantilevered finger 86 with an outwardly-projecting retention tab 88 on a proximal end thereof. Preferably there are a number of such cantilevered fingers 86 and tabs 88 around the circumference of the tubular housing 82 intermediate cantilevered sections of the tubular housing.

Figure 6A:
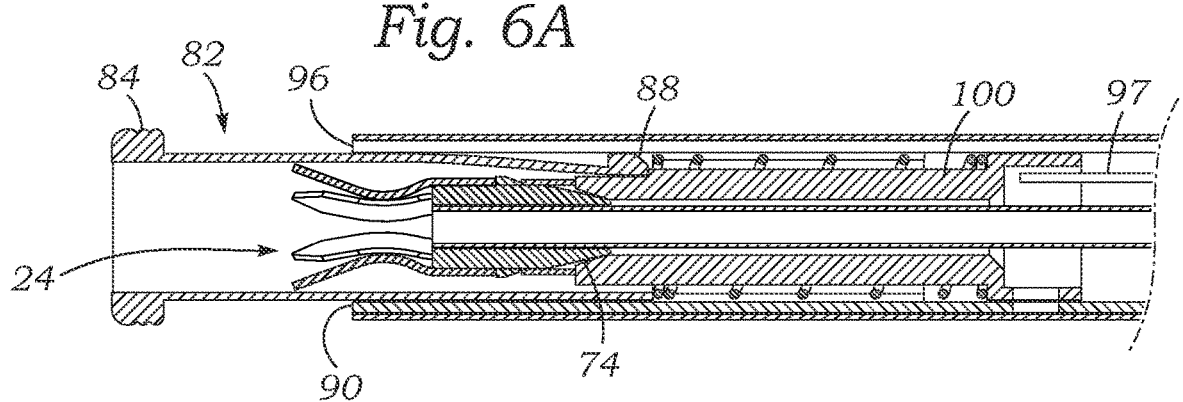
FIGS. 6A and 6B are sectional views of the alternative pressure regulating assembly showing removal of a lock preventing advancement of the tissue anchor.
Figure 6B:
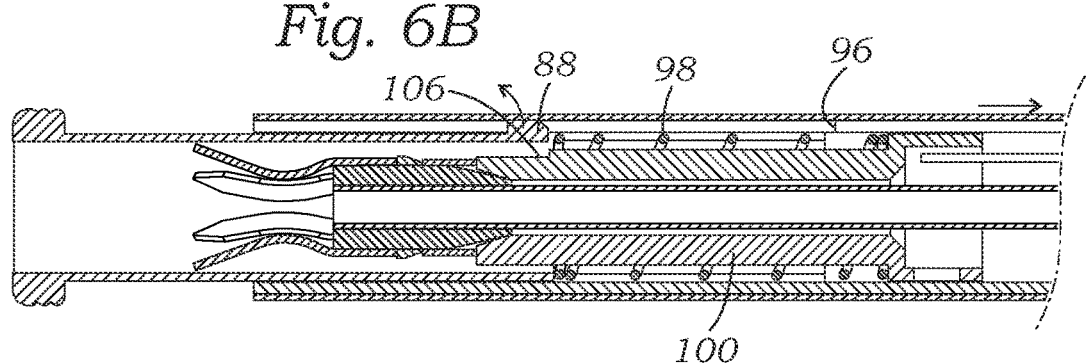

As seen in FIGS. 6A and 6B, the tissue anchor 24 on the distal end of the anchor rail 26 resides within the hollow tubular housing 82. The tubular housing 82 slides within a push-to-fire tubular frame 90 which has a longitudinal slot 92 cut into at least one side to interact with retention tabs 88 on the housing 82, as will be explained. The frame 90 has an outer tubular cover 94 which extends over the longitudinal slot 92, and also closely houses a coil spring 98. A lockout wire 96 extends through the longitudinal slot 92, and a pull wire 97 may be provided for steering the distal end of the catheter.

A generally tubular pusher 100 has a distal portion 102 that extends closely within the coil spring 98 and an enlarged proximal end that forms an annular shoulder 104 with the distal portion 102. A small step 106 at the distal end of the distal portion 102 provides a space within which the retention tab 88 may be biased, as will be explained.

FIGS. 6A and 6B are sectional views of the alternative pressure regulating assembly 80 showing removal of a lock that prevents advancement of the tissue anchor 24. It should be noted that the tubular frame 90 and pusher 100 may be adhered or welded to each other so as to move together, and the pull wire 97 is desirably welded to a proximal end of the pusher 100 on one side thereof. When the operator pulls the wire 97 such as from a proximal handle (not shown), the device bends or arcs in the same plane as the pull wire. Rotating the catheter about its axis enables steering in 360°. As mentioned above, although this steering mechanism is only shown in the embodiment of FIGS. 6A-6B, it may be incorporated into any other of the tissue anchoring catheter versions disclosed herein.

FIG. 6A shows the lockout wire 96 extended through the longitudinal slot 92 in the frame 92 to an approximate midpoint of the tubular housing 82. The wire 96 contacts the outwardly-directed retention tab 88, and thus biases it inward into engagement with the distal step 106 on the forward end of the pusher 100. Preferably, the retention tab 88 has a ramped outer proximal edge such that the lockout wire 96 may be easily inserted during assembly in a distal direction through the slot 92 and to cam the retention tab 88 inward. Because the retention tab 88 has a radial corner at the proximal end of the step 106, it prevents distal movement of the pusher 100 relative to the tubular housing 82. Furthermore, displacement of the pusher 100 is the sole means of advancing the tissue anchor 24 through the tubular housing 82 by virtue of engagement between a distal face of the pusher 100 and the tapered hub 74 of the tissue anchor 24. Consequently, the retention tab 88 prevents advancement of the tissue anchor 24 from within the tubular housing 82.

Once the catheter has been maneuvered such that the distal tip 84 is in contact with the target tissue, as can be verified with external visualization, the lock 96 may be released to enable advancement of the tissue anchor 24. FIG. 6B shows proximal retraction of the lockout wire 96, typically actuated from a proximal handle (not shown). This frees the retention tab 88 to flex outward as seen, out of engagement with the distal step 106 on the pusher 100. This in turn frees the pusher 100 to be displaced in a distal direction relative to the tubular housing 82.

Subsequently, forward or distal movement of the pusher 100 compresses the spring 98 between the shoulder 104 of the pusher 100 and the tubular housing 82. Although not shown, the pusher 100 compresses the spring 98 to a desired amount at the moment that the tissue anchor 24 reaches the open distal mouth of the tubular housing 82. Further advancement of the pusher 100 drives the tissue anchor 24 into the tissue, again with the desired amount of compressive force applied to the tissue. This configuration thus provides an automatic force regulation and tissue anchor deployment, coupled with a safety feature which prevents premature movement of the tissue anchor.

Figure 7A:
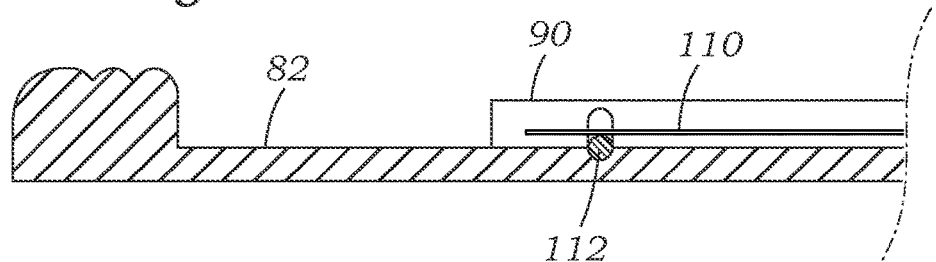
FIGS. 7A and 7B are schematic views of alternative locks.
Figure 7B:
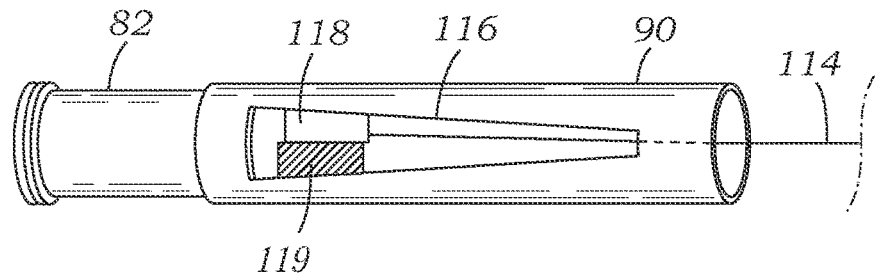
Figure 8A:
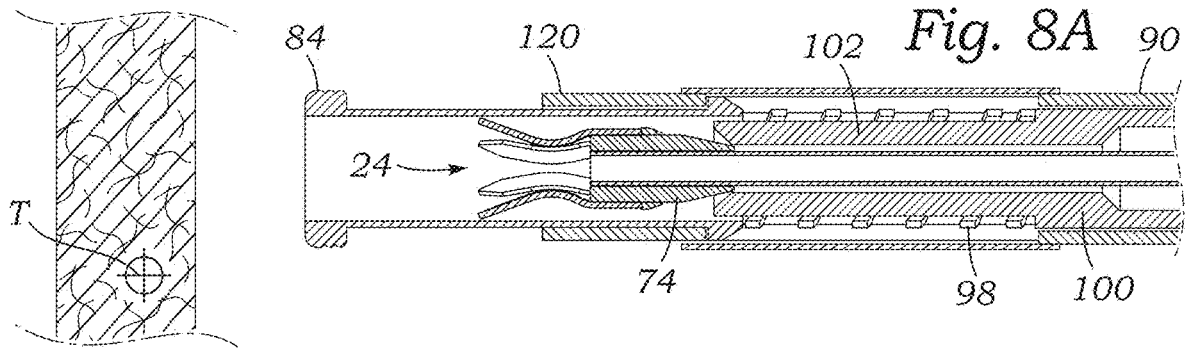
FIGS. 8A-8D are sectional views of steps in positioning a further alternative tissue anchoring catheter over a target tissue site which is a hybrid that combines pressure regulation an automatic tissue anchor deployment with visualization.
Figure 8B:
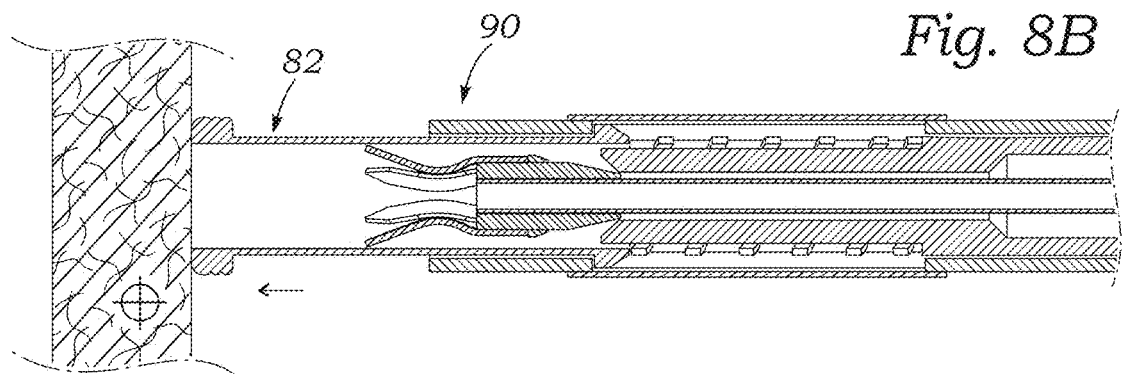
Figure 8C:
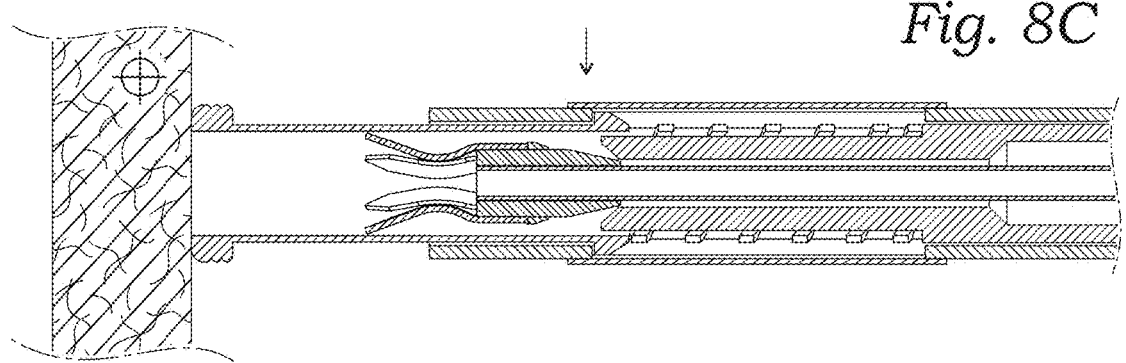
Figure 8D:
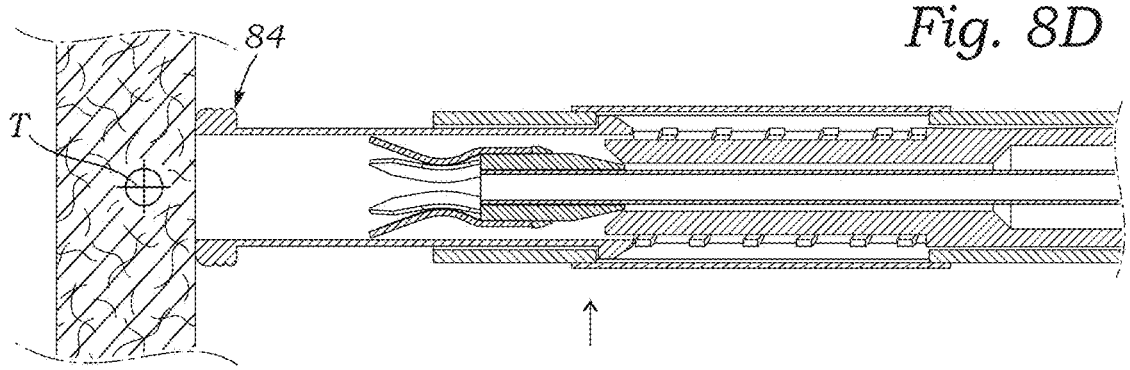

FIGS. 7A and 7B are schematic views of alternative locks that can be used to prevent premature movement of the tissue anchor. In FIG. 7A, a lockout wire 110 extends forward into engagement with a lockout ball 112 mounted to slide in and out of a channel formed within the housing frame 90 and forces the ball radially inward into a groove (not numbered) on the outside of the tubular housing 82. Since the housing frame 90 and pusher 100 are coupled together, the tubular housing 82 can be prevented from moving relative to the pusher 100 in the position shown. Retraction of the lockout wire 110 permits the lockout ball 112 to move outward into the channel in the frame 90, which permits relative movement of the tubular housing 82. Thus, the pusher 100 can move forward relative to the tubular housing 82 and eject the tissue anchor 24.

In FIG. 7B, a lock assembly includes a pull wire 114 that extends from proximal handle into an elongated opening 116 in the tubular frame 90. The pull wire 114 connects with a movable wedge member 118 that interacts with an outward tab 119 on the housing 82. By virtue of the shape of the opening 116, the wedge member 118 prevents movement of the tab 119, and thus locks the tubular housing 82 with respect to the housing frame 90. Retraction of the pull wire 114 disengages the wedge member 118 from the tab 119, thus permitting movement of the tubular housing 82 relative to the housing frame 90. Furthermore, numerous other locking mechanisms are contemplated.

FIGS. 8A-8D are sectional views of steps in positioning a further alternative tissue anchoring catheter over a target tissue site T. The assembly of components on the distal end of the catheter is similar to the assembly described above with respect to FIGS. 6A-6B except without a safety lock to prevent premature movement of the tissue anchor. Therefore, like elements will be given like numbers. In particular, a pusher 100 has a distal portion 102 that extends through the coil spring 98 and abuts a proximal end of the hub 74 of the tissue anchor 24. Displacement of the pusher 100 therefore also displaces the tissue anchor 24. Furthermore, the housing frame 90 is configured with a relatively thick radiopaque distal portion 120 that is used for visualization in conjunction with the thick distal ring 84 on the tubular housing 82. This configuration is thus a combination or hybrid of the distal assembly of components described with regard to FIGS. 3-4 having moving components that are easily visible using an imaging sensor/display, with the assembly of FIGS. 6A-6B wherein the tissue anchor 24 can be automatically deployed by simply displacing the pusher 100 in a distal direction. FIGS. 8A-8D shows several steps in advancing the catheter into contact with the tissue then repositioning the catheter until it is in alignment with the target site T.

Figure 9A:
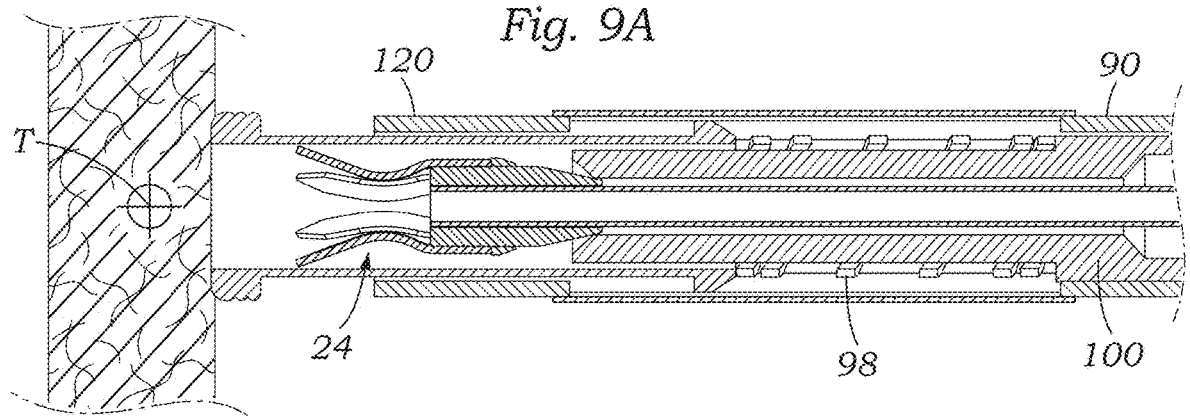
FIGS. 9A-9C are sectional views of steps of deploying the hybrid tissue anchor into the tissue using a pressure regulating assembly having an automatic deployment arrangement and visible indicators.
Figure 9B:
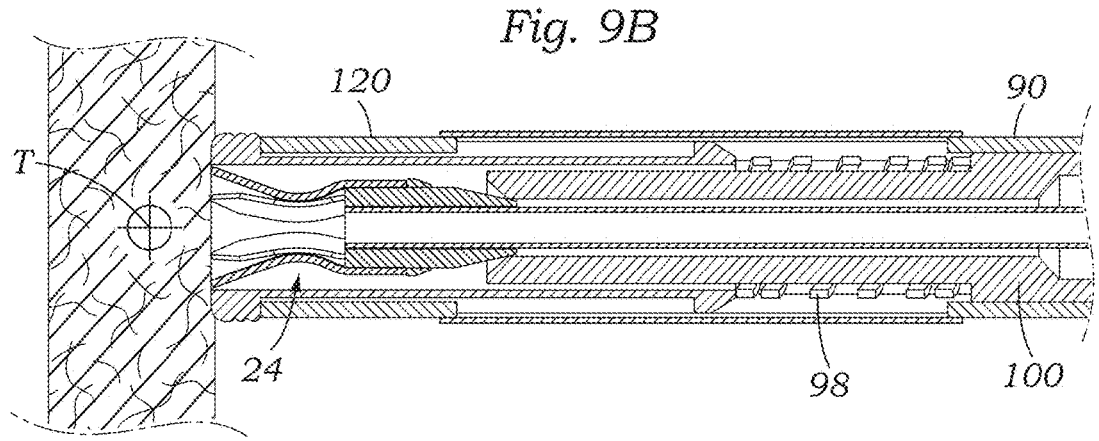

FIGS. 9A and 9B illustrate steps of deploying the hybrid tissue anchor of FIGS. 8A-8D into the tissue using a pressure regulating assembly having an automatic deployment arrangement as well as visible indicators. Once the target site T is reached, the operator advances the pusher 100 which advances both the tissue anchor 24 as well as the thick distal portion 120 on the housing frame 90. In FIG. 9B, the tines 30 of the tissue anchor 24 have reached the tissue surface, whereas the spring 98 is not fully compressed. This position of the tissue anchor 24 also corresponds to abutment of the radiopaque distal portion 120 of the housing frame 90 with the thick distal ring 84, which can easily be seen on an external display. At this point, the force applied to the tissue is calibrated such that further advancement of the tissue anchor 24 properly deploys it at the target site T. Such further advancement is done by distal movement of the pusher 100, until the spring 98 is fully compressed, in the automated "push-to-fire" configuration.

Figure 9C:
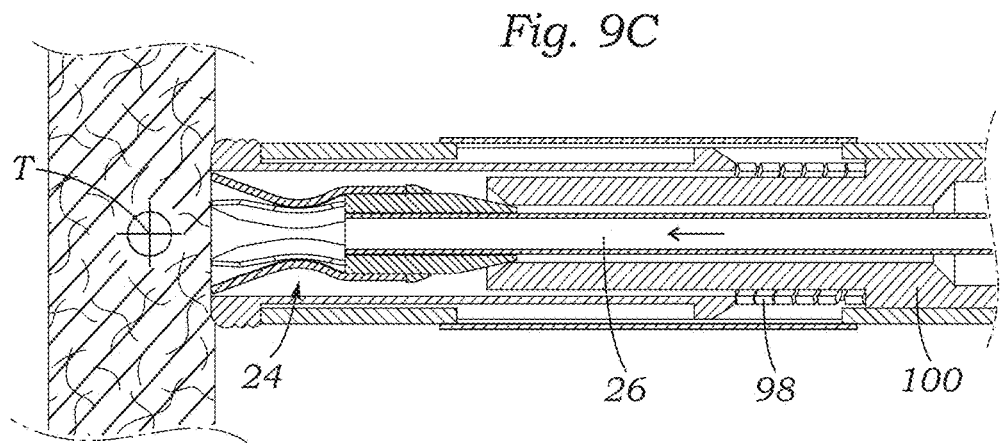

In an alternative embodiment, FIG. 9C shows the assembly with the tissue anchor 24 against the tissue surface, but with the spring 98 already fully compressed. In this configuration, further advancement of the pusher 100 is undesirable because it would just excessively press the entire assembly against the tissue and not eject the tissue anchor 24. Instead, advancement of the tissue anchor 24 is accomplished via separate advancement of the anchor rail 26, as described above. Consequently, this arrangement is not a fully automated anchoring method, even though the pusher 100 delivers the tissue anchor 24 to the tissue surface, and requires a separate movement of the anchor rail 26.

Visualization Alternatives

FIGS. 10A-10B are schematic views of the distal end of a tissue anchoring catheter of the present application showing different fluoroscopic images visible using an external imaging sensor of two positions of the pressure regulating assembly. The schematic views may correspond to several embodiments described above, such as the distal assembly 50 having a relatively movable tubular housing 52 relative to the housing frame 54. Upon contact of the thick distal ring 64 against tissue and further advancement of the frame 54, the thick-wall housing frame 54 shows up dark on the image display clearly abutting the dark distal ring 64. This signifies that the proper compressive force has been established between the catheter and the tissue, and that the tissue anchor and can be deployed.

Figure 11A:
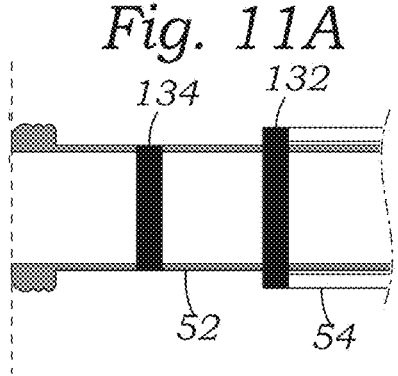
FIGS. 11A-11C are schematic views of different fluoroscopic images visible on an external imaging sensor of an alternative pressure regulating assembly in different positions.
Figure 11B:
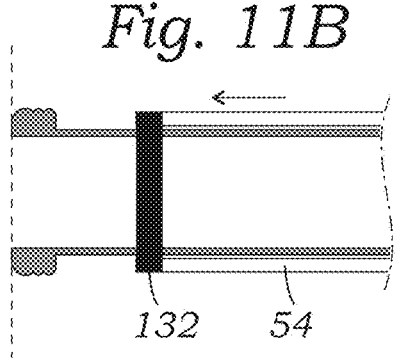
Figure 11C:
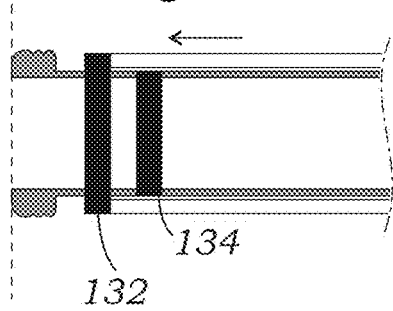

FIGS. 11A-11C are schematic views of fluoroscopic images visible on an external imaging sensor/display of an alternative pressure regulating assembly in different positions. In this instance, a movable sleeve that may form a part of the housing frame 54 includes a radiopaque band 132 on a distal end thereof. A tubular housing 52 that contacts the tissue may have a smaller radiopaque band 134 located at a mid-portion thereof. Advancement of the housing frame 54 as seen in FIG. 11B eventually aligns the radiopaque bands 132, 134, which signifies that proper compressive force has been established. FIG. 11C illustrates further advancement of the housing frame 54 which displaces the larger radiopaque band 132 distally passed the smaller band 134. This "overshoot" may signify that excessive force has been applied to the tissue, thus informing the operator to back off the housing frame 54.

Figure 12A:
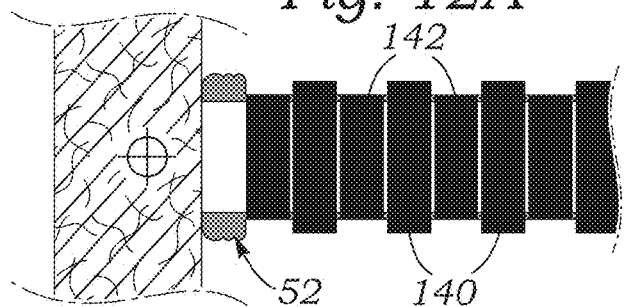
FIGS. 12A-12B are schematic views of fluoroscopic images visible on an external imaging sensor generated by a further alternative pressure regulating assembly.
Figure 12B:
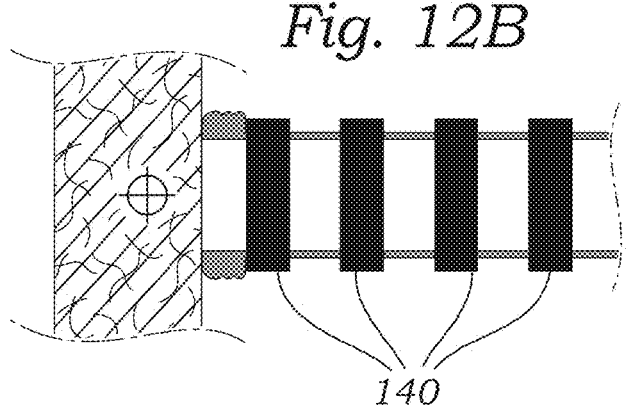

FIGS. 12A-12B are schematic views of fluoroscopic images visible on an external imaging sensor generated by a further alternative pressure regulating assembly. In this embodiment, an element such as the housing frame 54 described above may be provided with a series of circumferential radiopaque bands 140 that show up dark under fluoroscopy. Likewise, the tubular housing 52 defines a series of smaller circumferential radiopaque bands 142 that also show up as dark rings. Upon distal displacement of the tubular housing 52, the bands 140, 142 line up as in FIG. 12B, thus exhibiting an alternating dark and light pattern. This signifies to the operator that the proper compressive force has been reached. Additionally, numerous other radiopaque marker configurations are contemplated, and the embodiments disclosed should not be considered limiting.

In addition to providing visual indicators on the distal end of the catheter which can be monitored to determine when the proper force is applied to the tissue, other signals such as audio or tactile feedback may be used. For example, the various springs incorporated in the catheters disclosed herein may be replaced or supplemented by a strain gauge or piezo-electric sensor which transmits an electric current to the proximal end of the catheter upon being subjected to compressive force from contact with the tissue. The current can then be used to control an audio output, such as a tone with a gradually increasing volume or a series of tones which increase in frequency the closer to the desired compressive force. The current could also be used to eliminate a signal light when the proper compressive force is reached. Those of skill in the art will understand that these and various other indicators may substitute for or supplement the visual indicators disclosed herein.

Yet another solution is to incorporate a clutch mechanism of some sort at the distal tip of the catheter such that the operator can apply compressive force only up to the desired value after which the clutch mechanism slips and provides a tactile feedback to the operator. A clutch arrangement such as this provides a fail-safe pressure regulating mechanism.

Figure 13A:
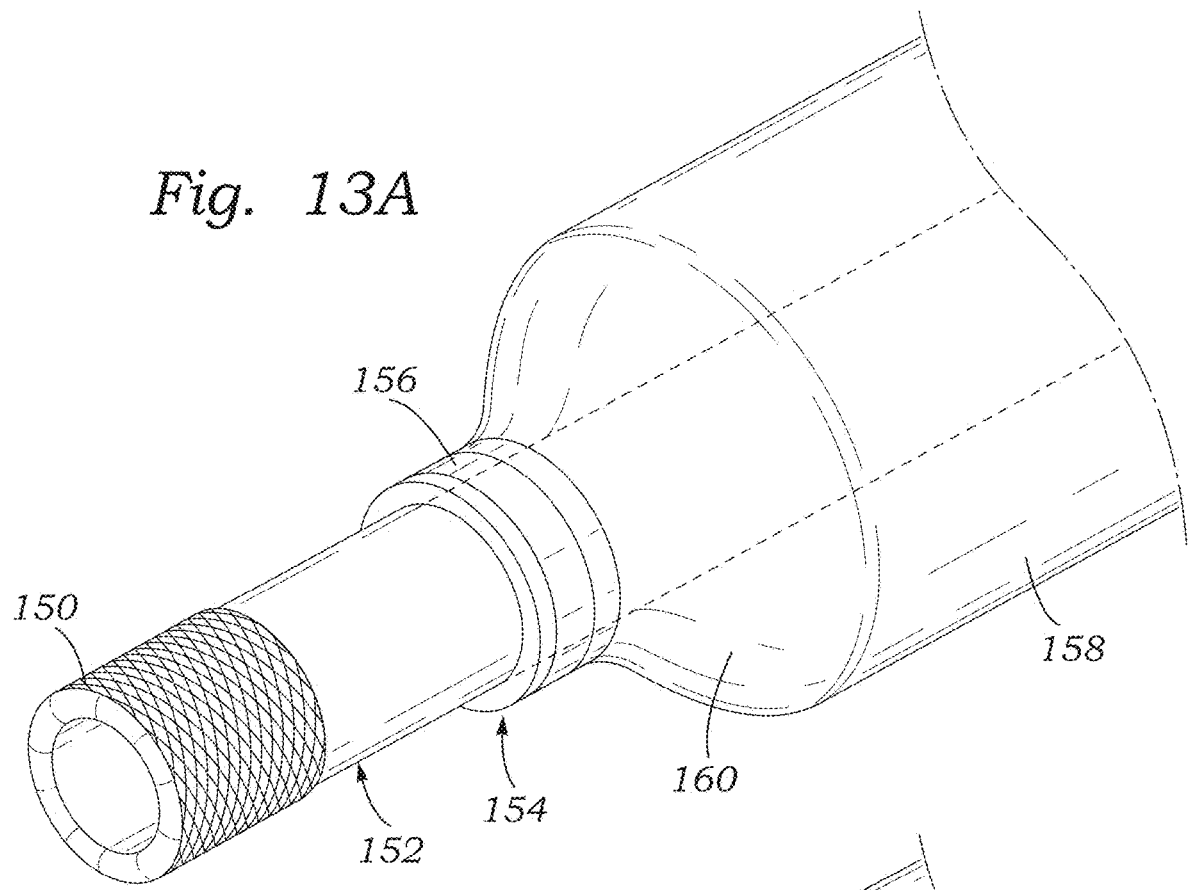
FIGS. 13A and 13B are perspective views of distal ends of tissue anchoring catheters showing alternative echogenic tips for high external visibility.
Figure 13B:
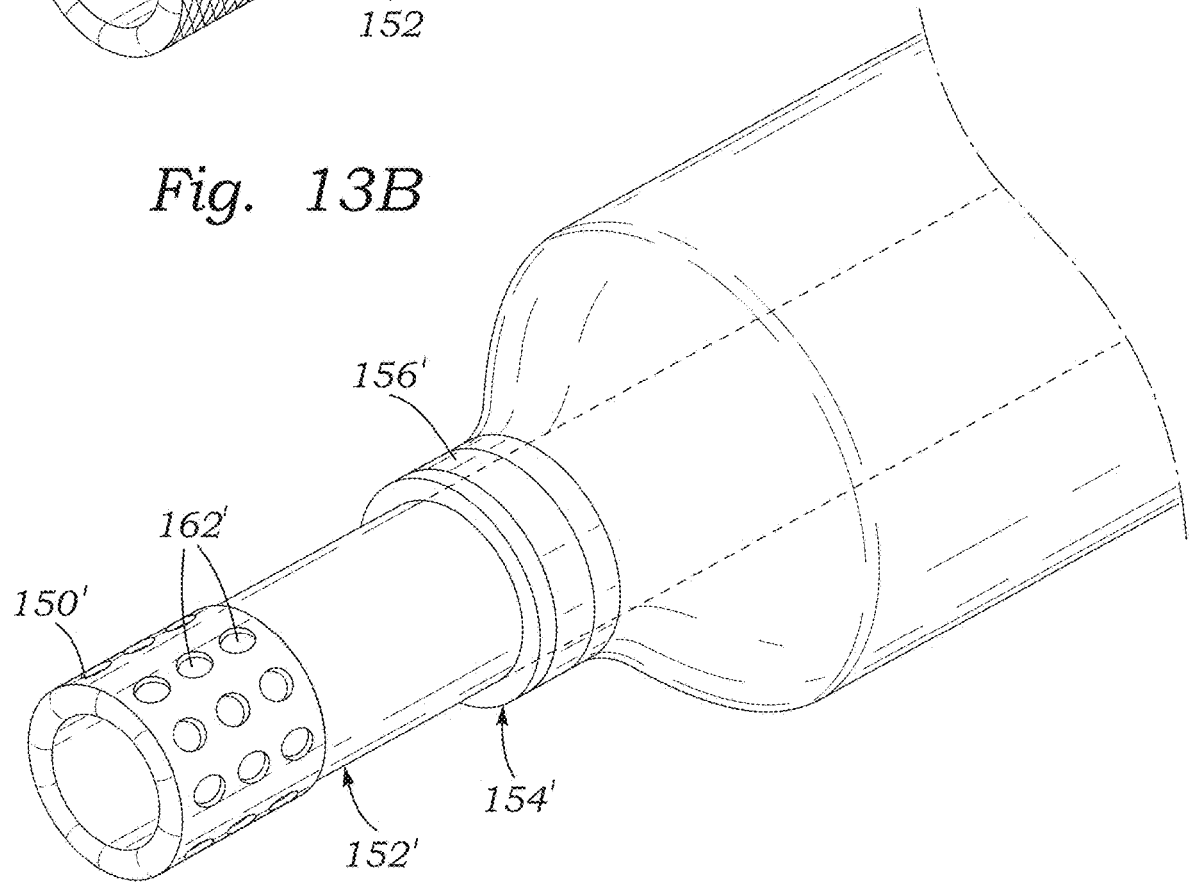

FIGS. 13A and 13B are perspective views of distal ends of tissue anchoring catheters showing alternative echogenic tips for high external visibility. In FIG. 13A, an echogenic distal tip 150 is provided at the distal end of a tubular housing 152, which may be the same as the tubular housing 52 described above with respect to FIGS. 2-3. Tubular housing 152 slides within a tubular housing frame 154, which again may be the same as housing frame 54. The frame 154 preferably has a radiopaque band 156 on a distal end thereof which shows up on an external imaging sensor/display relative to the echogenic distal tip 150. The distal tip 150 is shown having a knurled exterior which provides a plurality of crisscrossed reflective surfaces to increase radiopacity. A generally cylindrical guide balloon 158 having tapered ends 160 is shown mounted around the outside of the catheter.

FIG. 13B illustrates a similar structure with an echogenic distal tip 150' on the distal end of the tubular housing 152'. Again, a tubular frame 154' within which the housing 152' slides preferably has a radiopaque band 156' on a distal end thereof which shows up on an external imaging sensor/display relative to the echogenic distal tip 150'. In this embodiment, the tip 150' presents a series of round recesses or dimples 162' (which could also be formed as protrusions) that enhance the reflective nature of the tip. Of course, many other structures which improve the reflectivity of the catheter tips are contemplated, and the same structures can be added to the reflective bands 156, 156' on the housing frames, or any other surface which functions as a visibility indicator.

Spring Alternatives

Figure 14A:
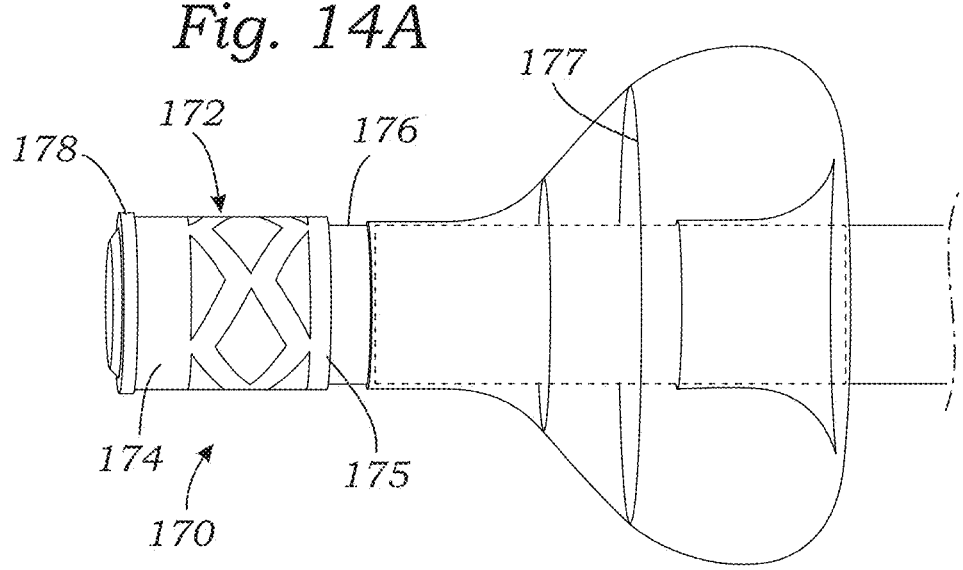
FIGS. 14A-14C are elevational views of alternative springs that may be used in the tissue anchor catheter pressure regulating assemblies.
Figure 14B:
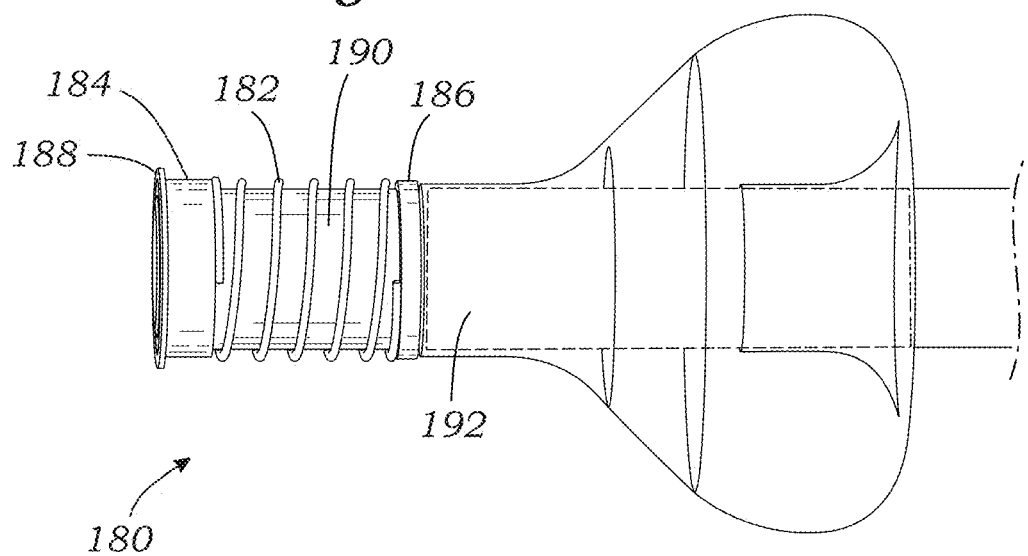
Figure 14C:
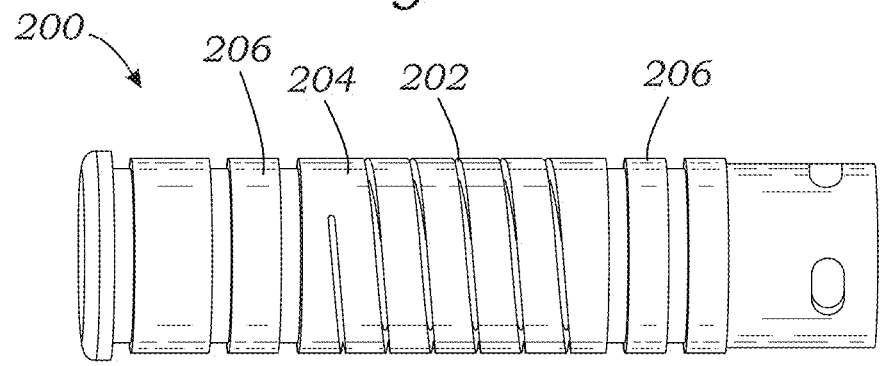

FIGS. 14A-14C are elevational views of alternative springs that may be used in the tissue anchor catheter pressure regulating assemblies in place of the internal coil springs disclosed above, such as that shown at 62 in FIG. 2. For instance, FIG. 14A illustrates an assembly of components at the distal end of a catheter 170 having an external spring member 172 formed from a tubular member 174 with a collapsible pattern cut into it, such as by using a laser. The tubular member 174 is made of a radiopaque material so as to be visible under fluoroscopy. A proximal end 175 of the tubular member 174 would be fixed to a shaft 176 extending from a distal end of a guide balloon 177. Although not shown, a movable tissue anchor is housed within the shaft 176. A distal end of the spring member 172 preferably has an enlarged ring 178 thereon which has enhanced visibility under fluoroscopy, or other such imaging technology. The enlarged ring 178 extends beyond a distal end of the shaft 176 so as to form a leading end of the catheter 170. When the catheter 170 is pressed against a tissue surface, the tissue exerts a proximal reaction force against the distal ring 178 which at a predetermined magnitude causes the spring member 172 to collapse. The relative proximal movement of the distal ring 178 and collapse of the spring member 172 shows up on the external sensor/monitor to notify the operator that a desired compressive force has been reached. As before, the structure of the spring member 172 is calibrated to collapse at a desired compressive force.

FIG. 14B shows an assembly of components at the distal end of a catheter 180 having an external spring member 182 welded between two external metal rings 184, 186. A distal ring 184 is highly visible under fluoroscopy and may have a radially wide distal flange 188 to broaden the tissue engagement surface and reduce the possibility of damage thereto. The distal ring 184 is desirably fixed around a tubular housing 190 that slides within a larger tubular housing frame 192 to which the proximal ring 186 is fastened. Advancement of the catheter 180 against the tissue surface thus displaces the tubular housing 190 in a proximal direction into the housing frame 192 against the bias of the spring 182. Again, the spacing between the two metal rings 184, 186 shows up clearly on fluoroscopy and can be used to determine when the proper compressive force is reached.

Finally, FIG. 14C illustrates an assembly 200 in which a compressive spring is formed by a spiral cut pattern 202 in a tubular member 204. The tubular member 204 extends between two radiopaque markers 206 which come together after the catheter 200 is pressed against tissue and the spring collapses.

Combined Spring and Visualization

FIGS. 15A-15E are sectional views of still further alternative springs formed by flexible plunger-like structures on the distal or leading end of the tissue anchor catheter that deform upon contact with tissue, and may also act as visual indicators such as being made from radiopaque material. As demonstrated by the alternative springs shown in FIGS.

14A-14C, there are a number of ways to establish a predetermined compressive force against the tissue into which the anchor is embedded. The present application contemplates internal and external coil springs formed as separate elements, springs that are cut into catheter tubing, elastomeric sleeves or other such compressible elements, as well as the plunger-like structures of FIGS. 15A-15E.

Figure 15A:
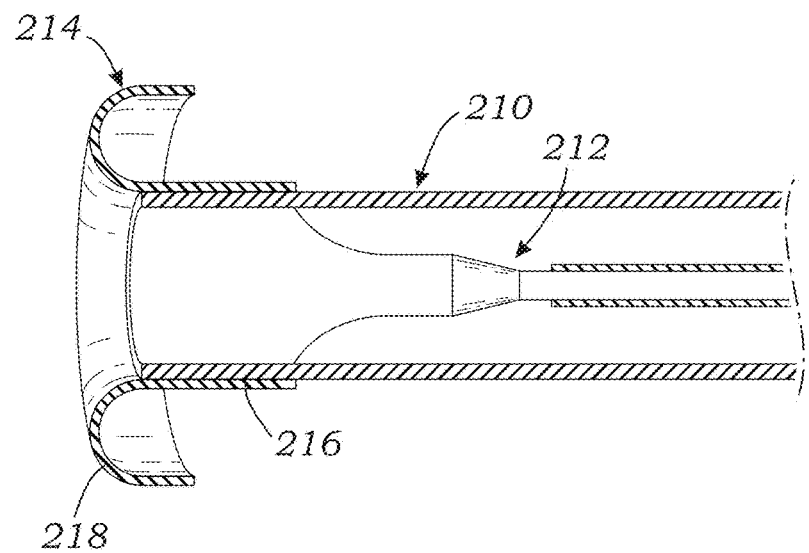
FIGS. 15A-15E are sectional views of still further alternative springs formed by flexible plunger-like structures on the distal end of the tissue anchor catheter that deform upon contact with tissue and may also act as visual indicators.

FIG. 15A shows a distal end of a tissue anchor catheter 210 having a lumen through which a tissue anchor 212 travels. A flexible plunger-like distal tip 214 attaches to the distal end of the catheter tube and extends beyond the tube so as to form the leading end. The distal tip 214 is desirably an elastomer having radiopaque properties, such as silicone with barium sulfate particles embedded therein. The distal tip 214 in its relaxed configuration as shown has a tubular collar 216 secured around the catheter 210 and a half-doughnut shaped flap 218 extending distally from the catheter and curving outward and back approximate 180°. Preferably, a portion of the catheter 210 adjacent the distal tip 214 is also radiopaque. When the catheter 210 is pressed against tissue, the flap 218 deforms in a proximal direction which movement relative to the catheter can be seen on a fluoroscope.

Figure 15B:
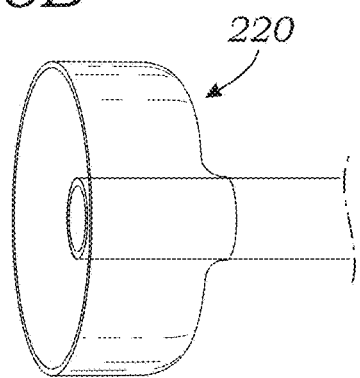
Figure 15C:
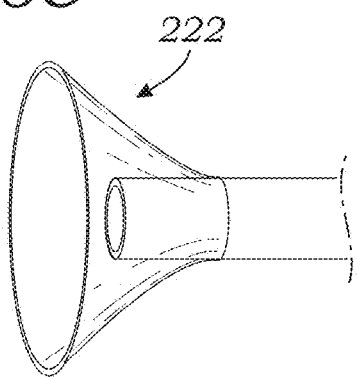
Figure 15D:
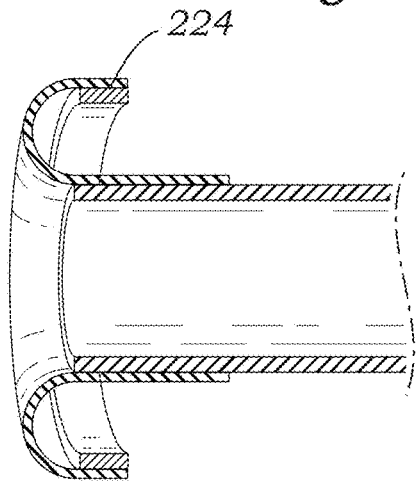
Figure 15E:
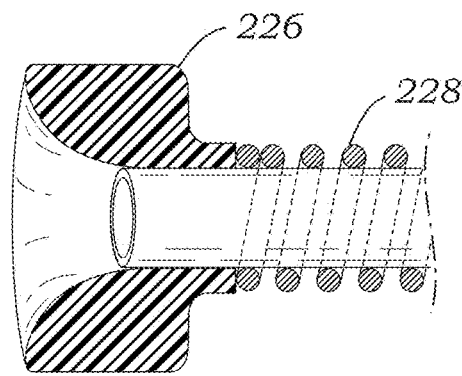

FIG. 15B illustrates an alternative plunger-like distal tip 220 which is also preferably elastomeric and radiopaque. The tip 220 has a proximal portion attached to the catheter and a distal portion in the shape of a forward-facing cup that forms a leading end of the catheter. Again, pressure against the tissue wall deforms the tip 220 which is seen on an external imager/display. An elastomeric/radiopaque distal tip 222 shown in FIG. 15C is formed in the shape of a trumpet horn such that pressure against a tissue wall causes the tip to flare outward in a proximal direction. The elastomeric tip shown in FIG. 15D is somewhat similar to the tip 214 of FIG. 15A but also includes a radiopaque ring 224 embedded around a proximal edge. Movement of the radiopaque ring 224 shows up readily on the external imager display. Finally, FIG. 15E shows a soft or flexible annular tip 226 disposed on and forming a leading end of the catheter which is biased in a distal direction by a coil spring 228. The tip 226 may not deform to the extent of the previously-described plunger-like tips, but is radiopaque and may be pushed backward upon contact with the tissue surface against the bias of the spring 228. Movement of the tip 226 thus indicates the level of force applied by the catheter against the tissue. Desirably, the tip 226 has a front face that has rounded surfaces and corners, such as the trumpet-like shape shown.

Figure 16A:
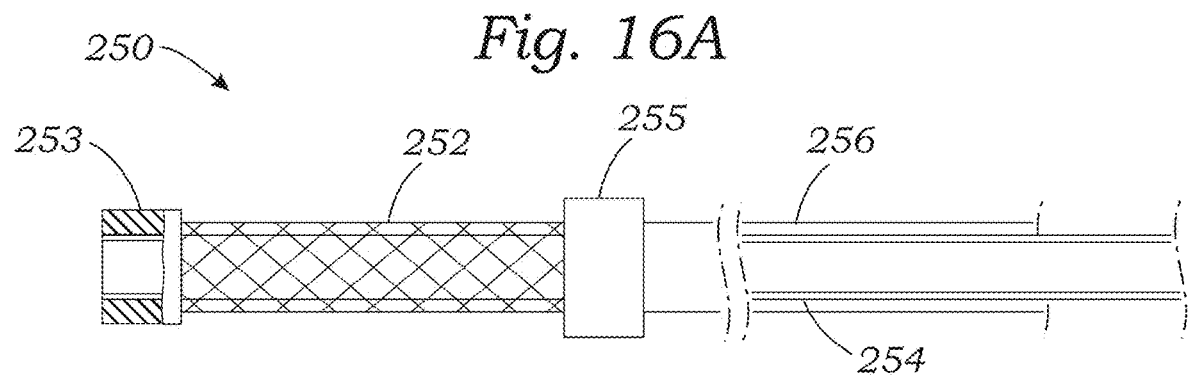
FIGS. 16A-16C are sectional and elevational views of an alternative pressure regulating assembly for the tissue anchor catheters of the present application that utilizes an external braided structure that expands radially outward when axially compressed.
Figure 16B:
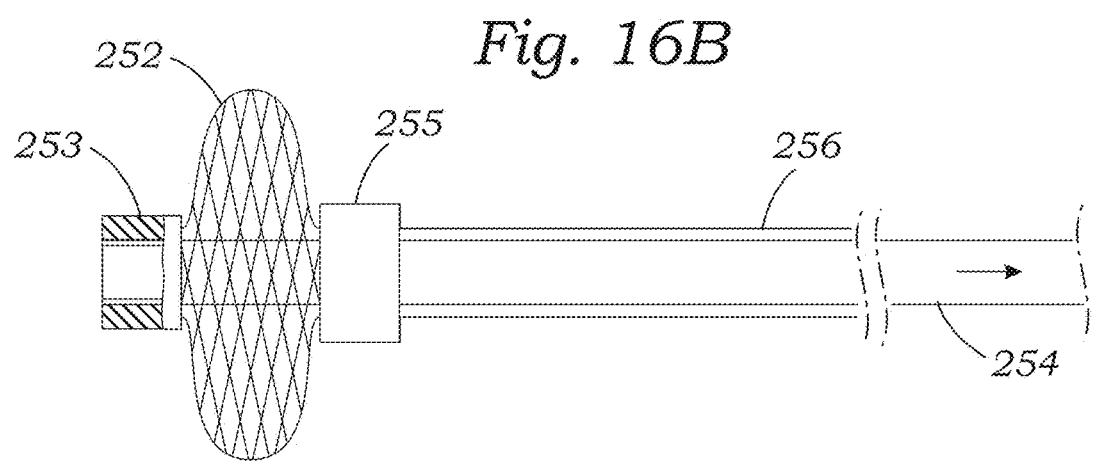
Figure 16C:
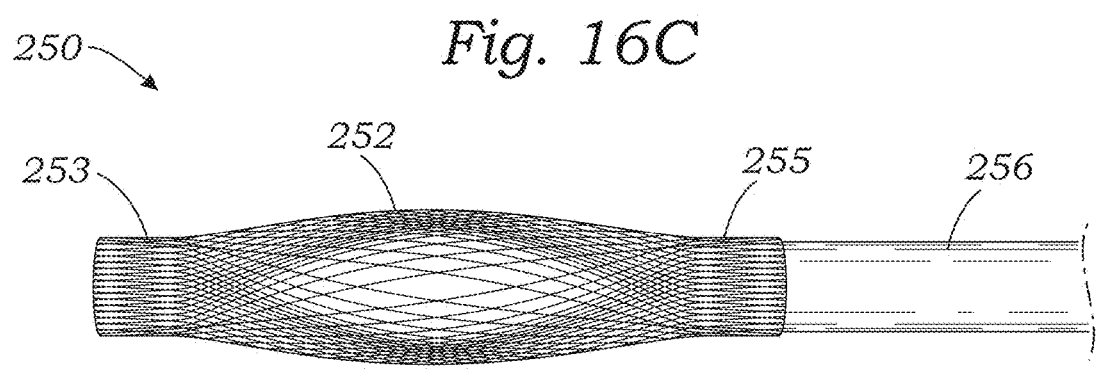

FIGS. 16A-16C illustrate a still further alternative pressure regulating assembly for the tissue anchor catheters of the present application. In a tissue anchoring catheter 250, an exterior expandable braided tube 252 typically made of Nitinol attaches at a distal end 253 around an inner shaft 254, and at a proximal end 255 around an outer shaft 256. The braided tube 252 can be converted from a relatively narrow delivery configuration seen in FIG. 16A to an expanded configuration seen in FIG. 16B by proximally displacing the inner shaft 254 relative to the outer shaft 256. This displacement of the inner shaft 254 can be a result of contacting the distal end 253 against tissue just prior to deploying an anchor (not shown). The braided tube 252 possesses an elasticity that requires a particular force to compress it to the expanded configuration, which force can be calibrated to correspond to a desired compressive force against the tissue. Expansion of the braided tube 252 can be detected through various means as described herein, including simply forming the tube from a radiopaque material such as Nitinol or providing radiopaque markers thereon and monitoring its shape. Alternatively, the ring-shaped distal end 253 and proximal end 254 may be radiopaque such that the operator can monitor their relative axial spacing via an external imager as an indicator for when the braided tube 252 expands and shortens axially.

FIG. 16C illustrates a prototype of the expandable braided Nitinol or polymer mesh tube 252 at the distal end of the catheter 250. In addition to providing the pressure regulating function for the tissue anchor as described herein, the braided tube 252 can substitute for the guide balloon used to assist in advancing the anchoring catheter to the target location. Conventional guide balloons, such as the guide balloon 28 shown in FIGS. 1A-1B, are inflatable polymeric structures that must be leak tested prior to use. Substitution of the expandable braided tube 252 eliminates the possibility of leaks and thus is more reliable and facilitates manufacture by obviating any leak testing. The braided tube 252 can be converted to its expanded configuration by providing control of the inner shaft 254 relative to the outer shaft 256 from a proximal handle (not shown).

Figure 17A:
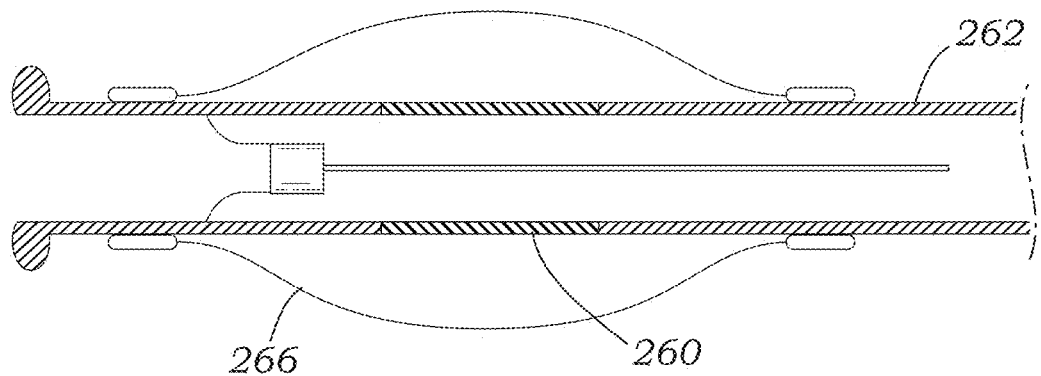
FIGS. 17A and 17B illustrate an alternative pressure regulating assembly including an internal bellows-like structure in two different positions.
Figure 17B:
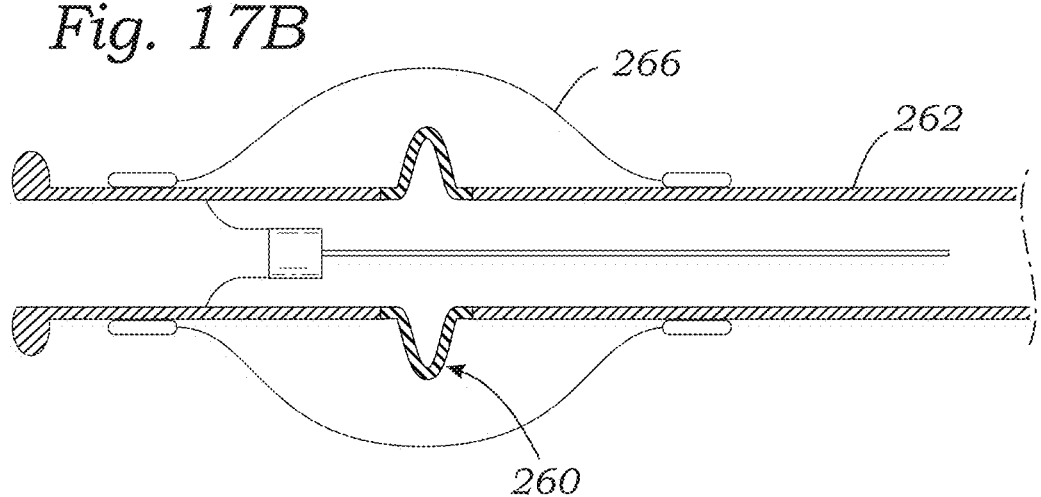
Figure 17C:
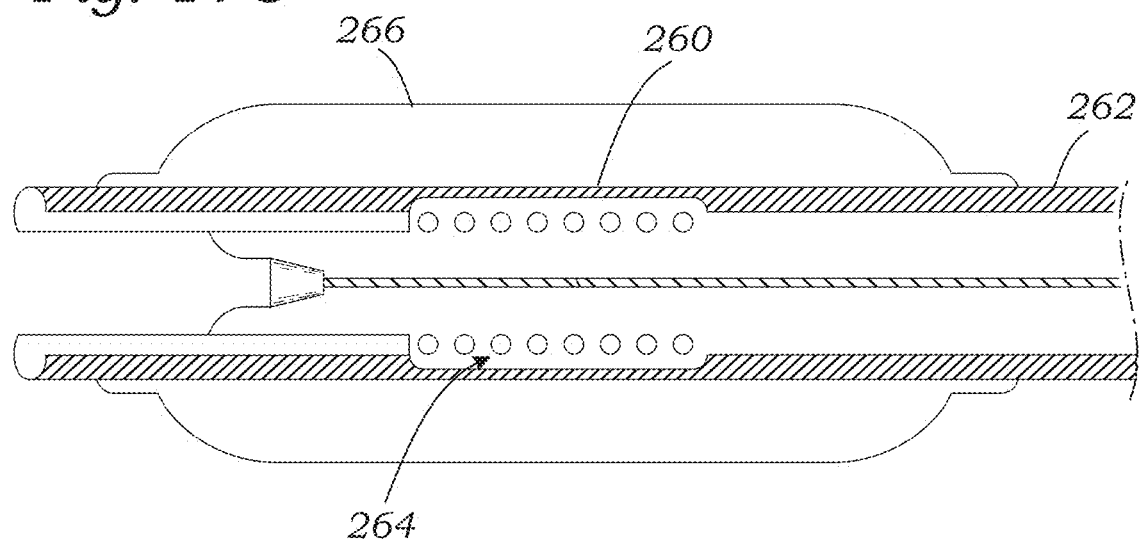
FIG. 17C shows an internal spring that may incorporate radiopaque markers.

FIGS. 17A and 17B illustrate an alternative pressure regulating assembly including an internal bellows-like structure 260 in two different positions, and FIG. 17C shows an internal spring that may incorporate radiopaque markers. The bellows-like structure 260 may be constructed from a segment of different tube as in FIGS. 17A and 17B, or as seen in cross-section in FIG. 17C as a thin section in an elongated catheter shaft 262. The bellows-like structure 260 bows outward when the shaft 262 is compressed against the tissue, as seen in FIG. 17B. An internal spring 264 shown in in FIG. 17C may be situated in the recessed area created by the thin-walled structure 260 and provides resiliency and spring back to straighten the catheter shaft 262 when compression ends. The spring 264 may also be radiopaque or have markers thereon to enhance the visualization of the compressed catheter. A guide balloon 266 is shown surrounding the distal end of the catheter 262, and may be bulbous in shape as in FIGS. 17A and 17B, or more cylindrical as in FIG. 17C.

Preliminary Tip Retraction

A number of the pressure regulators described herein rely on a spring-biased distal end of the catheter shaft which retracts into the main portion of the catheter when pushed against tissue. These devices tend to elongate the distal end of the device beyond the guide balloon, which is not desirable because the distal tip can become entangled with anatomical structures or cause damage if inadvertently maneuvered into delicate tissues. Consequently, the present application contemplates several solutions described below.

Figure 18A:
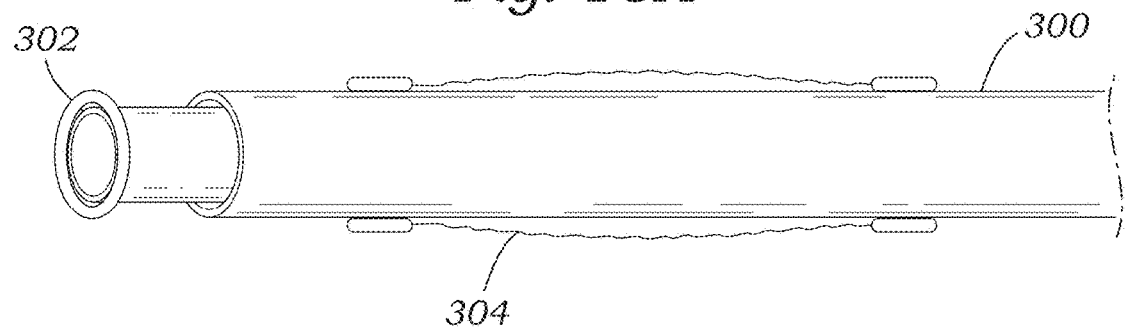
FIG. 18A is a schematic view of the distal end of an exemplary tissue anchor catheter of the present application showing extension of spring-loaded tip.
Figure 18B:
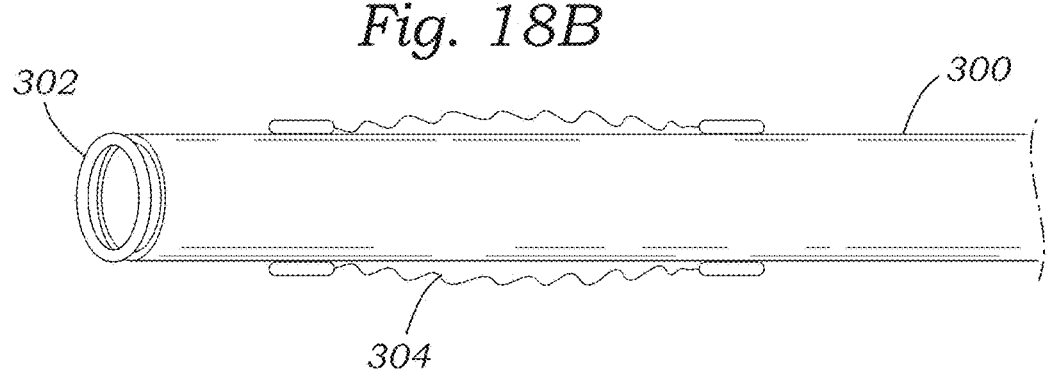
FIG. 18B is a schematic view of a preferred retracted position of the spring-loaded tip during delivery.

FIG. 18A is a schematic view of the distal end of an exemplary tissue anchor catheter 300 of the present application showing extension of spring-loaded tip 302. FIG. 18B is a schematic view of a preferred retracted position of the spring-loaded tip 302 during delivery. A guide balloon 304 is shown on the exterior of the catheter 300. The extension of the tip 302 beyond the balloon 304 as in FIG. 18A is preferably minimized by retracting or "choking up" on the tip 302 to the position of FIG. 18B.

Figure 19A:
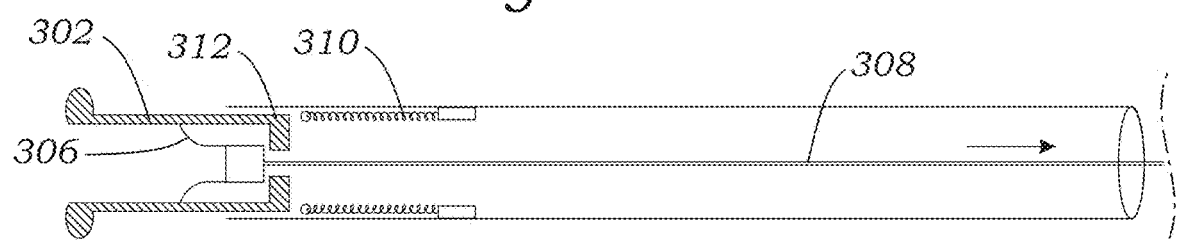
FIGS. 19A and 19B are schematic views of two different solutions for enabling retraction of the spring-loaded tip as in FIG. 18B.
Figure 19B:
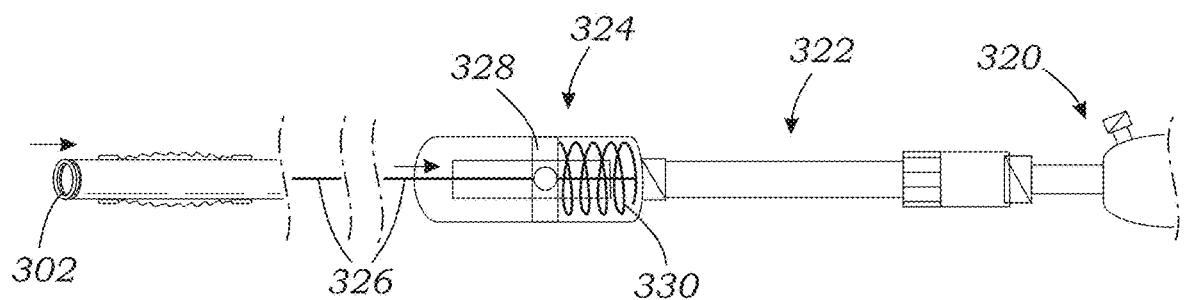

FIGS. 19A and 19B are schematic views of two different solutions for enabling retraction of the spring-loaded tip 302 as in FIG. 18B. In the example of FIG. 19A, a tissue anchor 306 is shown held within the tubular tip 302 with an anchor rail 308 extending proximally therefrom. A spring 310 that can also be used for the force regulation, or may be a secondary spring, is located within the catheter tube 300 just proximal to the tip 302. By virtue of stops 312 within the spring-loaded tip 302, the tip can be retracted by pulling in a proximal direction on the anchor rail 308. In one embodiment, the anchor rail 308 may be retracted using a control on a proximal handle (not shown) and held in the retracted position. This retracts or "chokes up" the tip 302 during delivery of the catheter 300 to reduce the extent of the catheter beyond the external guide balloon (not shown in FIG. 19A). Once the distal end of the catheter is maneuvered into position adjacent the tissue target site, the anchor rail 308 is released to extend the spring-loaded tip 302, and the aforementioned force regulation step can be performed.

FIG. 19B illustrates one exemplary tissue anchoring catheter having a proximal handle 320, a pusher shaft 322, an anchor rail tensioner 324, and an anchor rail 326 which extends to a distal end of the catheter (not shown). A proximal end of the anchor rail 326 fastens to a carriage 328 arranged for sliding movement within the rail tensioner 324. The carriage 328 is biased by a spring 330 within the rail tensioner 324 in a proximal direction. In this manner, the anchor rail 326 is biased in a proximal direction, which pulls the distal tip 302 into the catheter tube by virtue of its interaction with the tissue anchor therein (similar to anchor 306 in FIG. 19A). After the catheter is maneuvered into position adjacent the tissue target site, the operator advances the pusher shaft 322 which extends the distal tip 302. After contact with tissue, the rail spring 330 pulls the distal tip 302 back into the catheter shaft against the bias of a force regulation spring (not shown) as described above.

Figure 20A:
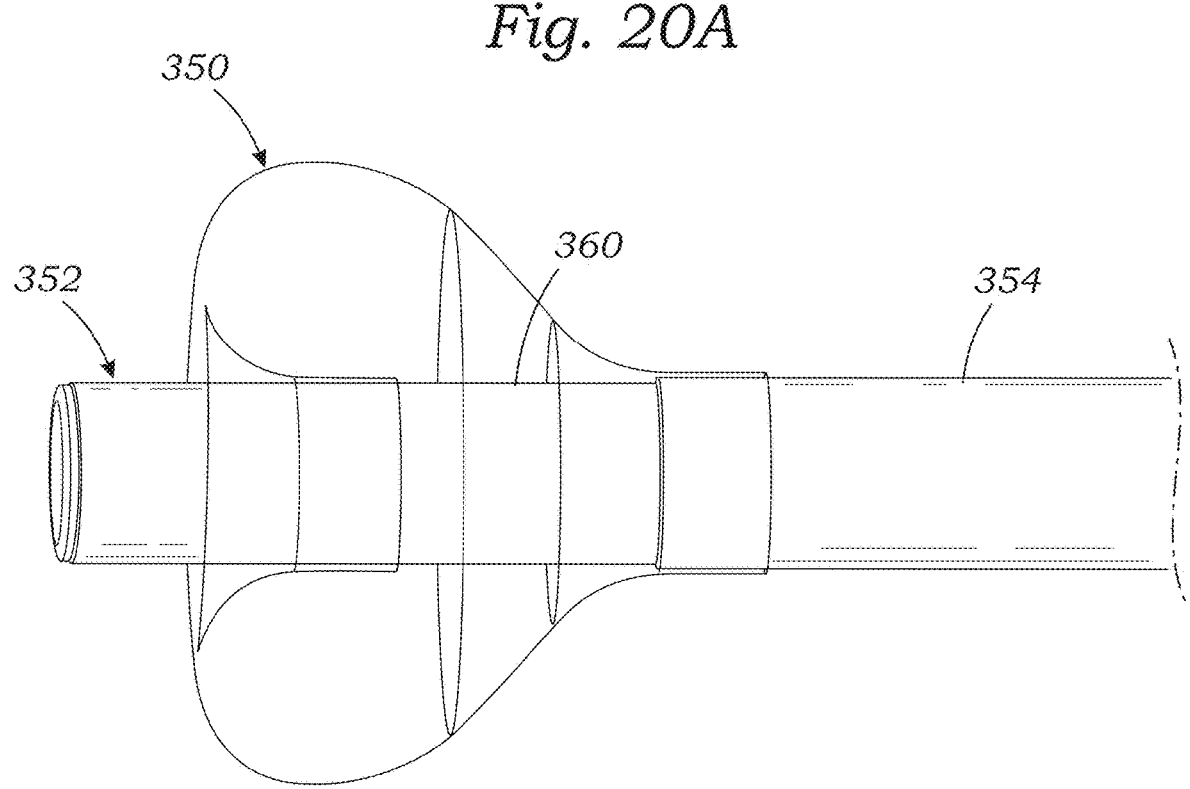
FIG. 20A is an elevational view of an alternative positioning balloon for use on the distal end of the tissue anchor catheter which is inverted to reduce the extent of the catheter that projects distally from the balloon.
Figure 20B:
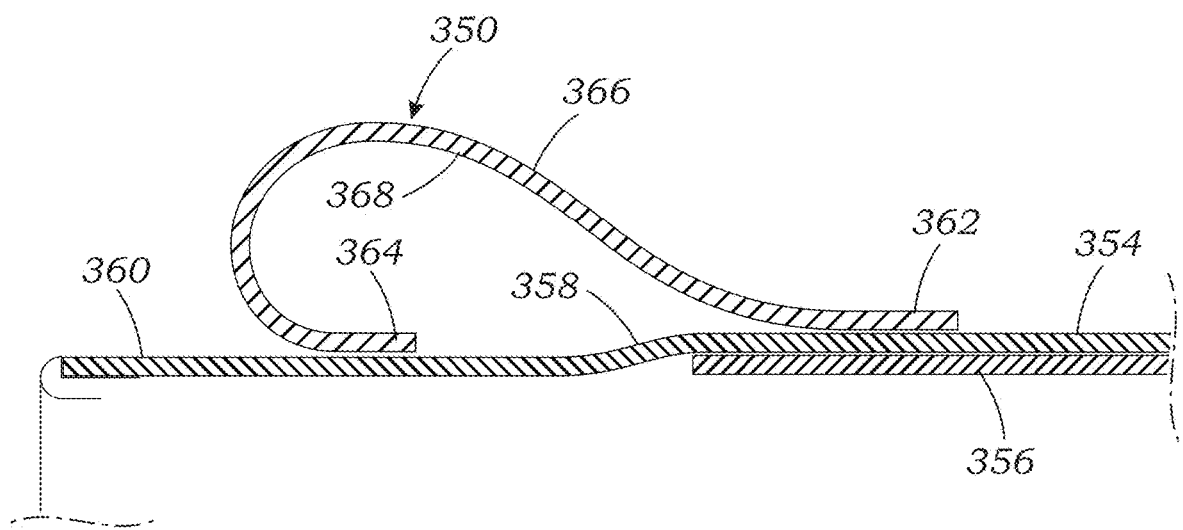
FIG. 20B is a sectional view through one sidewall of the tissue anchor catheter of FIG. 20A.

FIGS. 20A and 20B show one arrangement for a guide balloon 350 attached to the exterior of the distal end of a tissue anchor catheter 352 to reduce the extent of the catheter that projects distally from the balloon. The shaft of the catheter has an enlarged proximal portion 354, such as by virtue of placing a tubular spacer 356 therein. The shaft 354 reduces in diameter at step 358 to a narrower distal portion 360. A proximal collar 362 of the balloon 350 attaches to the larger proximal portion 354, while a distal collar 364 attaches to the smaller distal portion 360 after having been inverted. That is, the balloon 350 has an exterior surface 366 and an interior surface 368. The proximal collar 362 is formed by adhering the interior surface 368 to the outside of the catheter shaft, while the distal collar 364 is formed by inverting the balloon material and adhering the exterior surface 360 to the outside of the catheter shaft. This method of construction causes the balloon 350 to have an enlarged or bulged distal end which effectively reduces the length of the catheter 352 that projects distally therefrom. This helps prevent contact of the distal tip of the catheter with cardiac tissue which can cause damage thereto.

The techniques described herein for successfully installing anchors in tissue by regulating the pressure applied by an installation tool are of course transferrable to implant systems other than the ones described above. Indeed, unless limited by any one claim, the devices and methods disclosed herein are applicable to any surgical or minimally-invasive anchoring solution. The example above of anchoring a tissue anchor 24 on the distal end of a tissue anchor rail 26 for use in a coaptation system for reducing regurgitation through a native valve is particularly salient as the motion of the ventricle in which the anchor is placed creates issues for successful anchoring. However, other locations in the body which undergo movement are good candidates for the anchoring techniques. Below is a discussion of one such usage, implanting an annuloplasty ring with a plurality of anchors, though it will be understood that this represents just one of many potential applications, and the target location need not even be one that experiences post-implant motion. Indeed, the type of anchor or the character of the tissue into which the anchors are placed may also be a factor that affects whether the techniques described herein are beneficial.

Figure 21A:
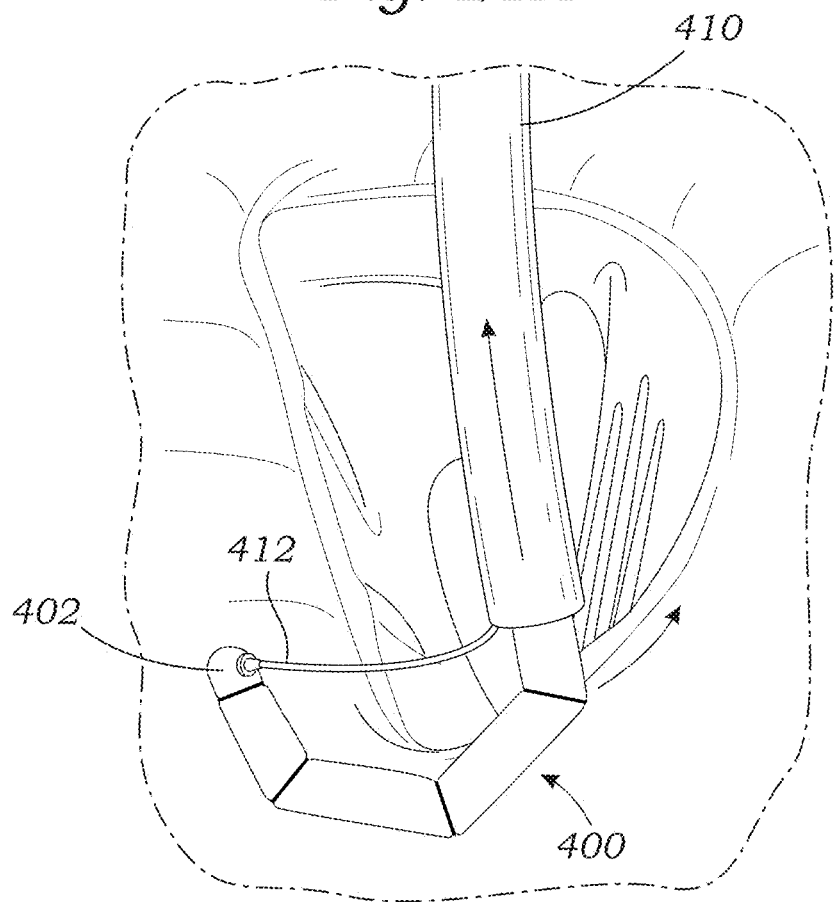
FIG. 21A is a perspective view of a partial implant of an annuloplasty ring around a mitral annulus using the techniques described herein.
Figure 21B:
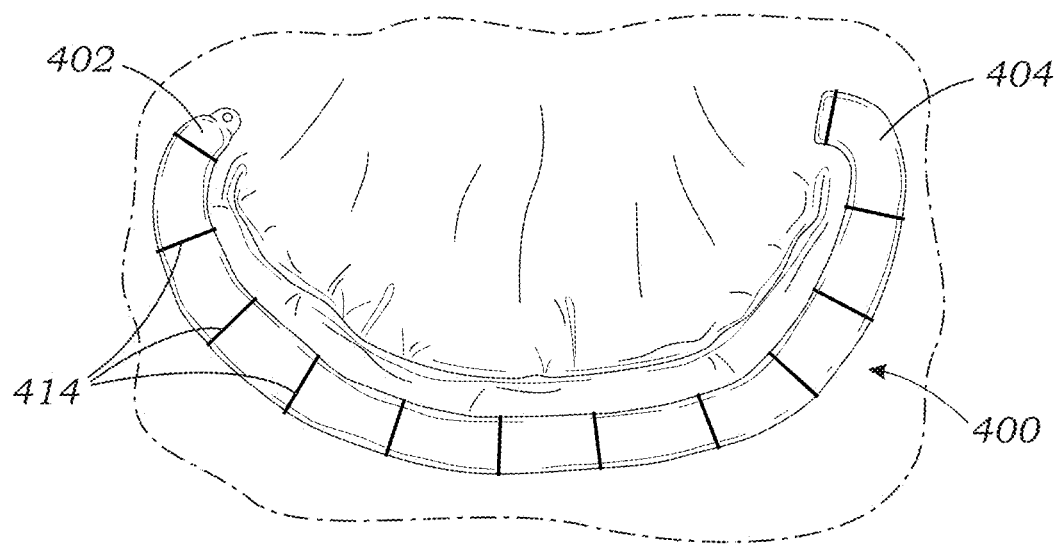
FIG. 21B shows the annuloplasty ring fully implanted.

FIG. 21A is a perspective view of a partial implant of an annuloplasty ring 400 around a mitral annulus using the techniques described herein, and FIG. 21B shows the annuloplasty ring fully implanted. The particular annuloplasty ring 400 and deployment procedure are similar to those disclosed in U.S. Pat. No. 9,119,719 to Zipory, the contents of which are expressly incorporated herein by reference. A commercial version of such an annuloplasty ring 400 that utilizes the same deployment procedure is sold under the trade name Cardioband Mitral System by Edwards Lifesciences Corp. of Irvine, Calif. It should be noted that the devices described in the following paragraphs may equally be used to treat the tricuspid valve or generally any of the heart valves.

The annuloplasty ring 400 is an open ring with two free ends 402, 404 and a middle portion 406 that, when fully implanted, extends roughly 270° around the mitral annulus, or generally around the posterior aspect to the annulus trigones. The annuloplasty ring 400 is installed through a sheath or catheter 410 which allows deployment through the patient's vasculature with the heart beating to reduce trauma to the patient. As set forth in U.S. Pat. No. 9,119,719, a first free end 402 is first expelled from the catheter 410 and anchored to the annulus. Sequential segments of the flexible annuloplasty ring 400 are then anchored, one-by-one, as the rest of the ring is expelled from the catheter 410. A control wire 412 that extends the length of the catheter 410 attaches to the first free end 402 of the ring and is used to create the forces needed to feed the ring around the annulus and gradually expel it from within the catheter. In the illustrated embodiment, the annuloplasty ring 400 has a series of marker bands 414 along its length that delineate the segments of the ring, each of which is fastened by a tissue anchor (not shown).

Figure 22:
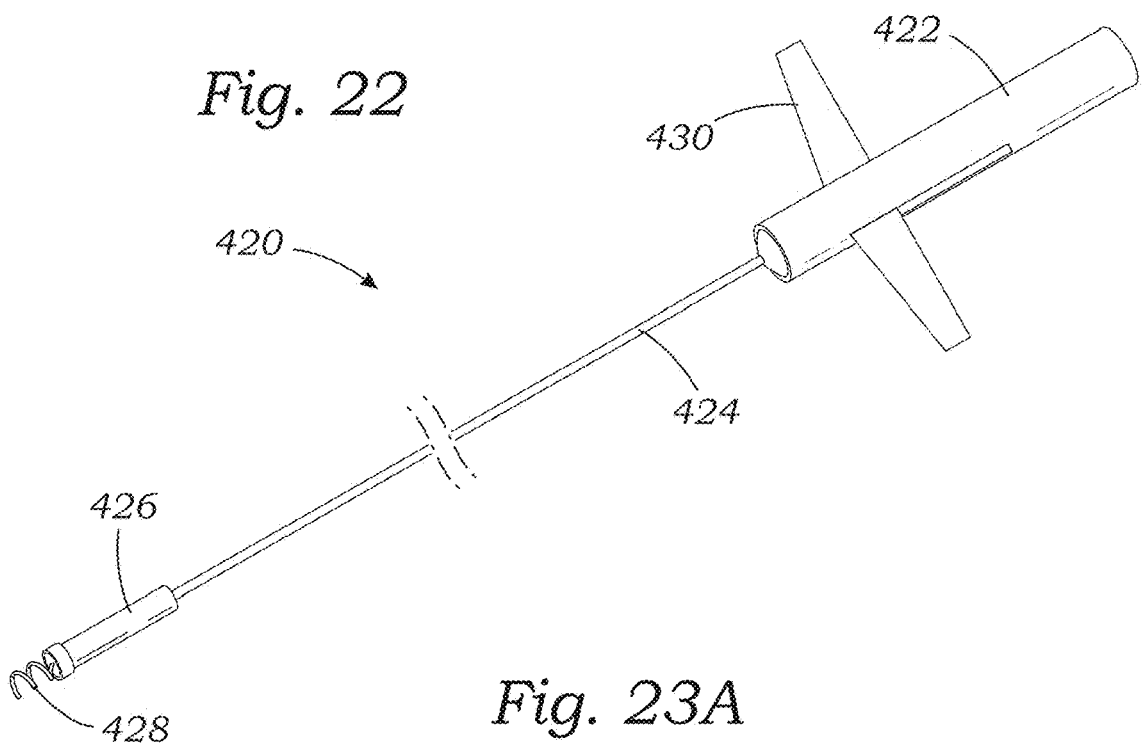
FIG. 22 shows one exemplary tool for installing a tissue anchor that can be used to implant the annuloplasty ring as seen in FIGS. 21A and 21B.

FIG. 22 shows one exemplary tool 420 for installing a tissue anchor that can be used to implant the annuloplasty ring as seen in FIGS. 21A and 21B. The tool 420 comprises a proximal handle 422 having an elongated flexible shaft 424 connected thereto and extending distally to an anchor driver 426. A corkscrew-like tissue anchor 428 is shown held by the anchor driver 426. The handle 422 preferably includes a pair of opposed tabs 430 that, along with the shaft 424, enable a user to apply torque to the anchor driver 426 and thereby screw the tissue anchor 428 into tissue. The opposed tabs 430 may also be mounted for pivoting or axial movement relative to the handle 422 to actuate a release mechanism (not shown) that decouples the tissue anchor 428 from the anchor driver 426.

Figure 23A:
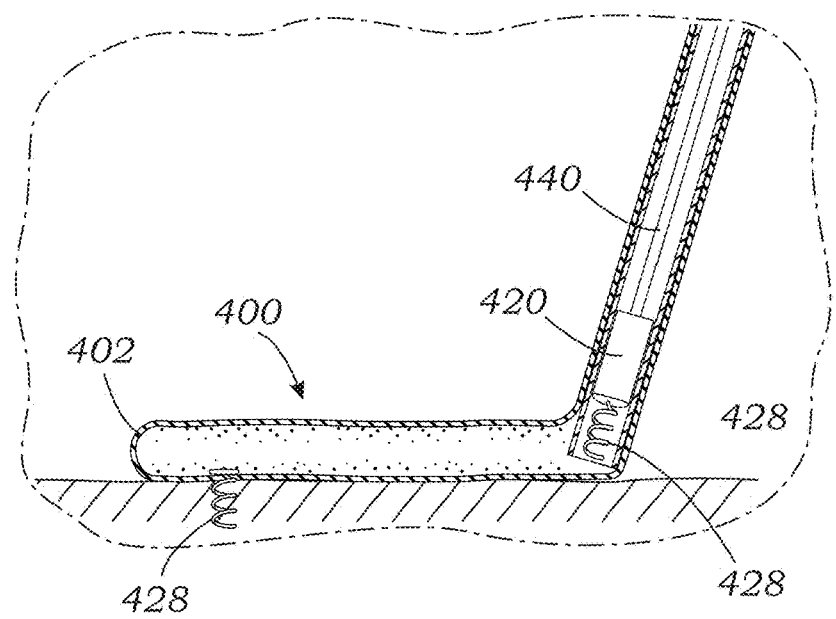
FIGS. 23A and 23B are sectional views through a sleeve-like annuloplasty ring showing use of the tool of FIG. 22 to install tissue anchors.
Figure 23B:
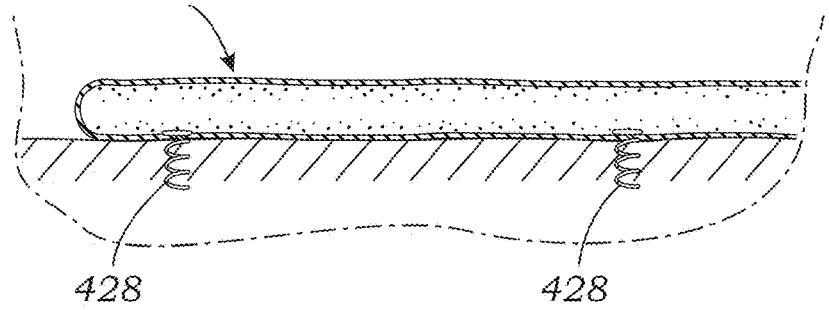

FIGS. 23A and 23B are sectional views of an annuloplasty ring 400 being implanted. The tool 420 of FIG. 22 is used to install a plurality of tissue anchors 428 through a side wall of the ring 400 and into tissue. More particularly, the tool 420 with a tissue anchor 428 thereon is passed through a flexible anchor catheter 440 of the present application that extends through a hollow interior of the sleeve-like annuloplasty ring 400. As explained in U.S. Pat. No. 9,119,719, a plurality of anchors 428 are applied using the tool 420 by loading a first one of the anchors onto the anchor driver 426, and deploying the anchor into the cardiac tissue. The tool 420 may then be withdrawn from the subject's body (typically while leaving anchor catheter 440 in place in the annuloplasty ring 400), and a second one of the anchors 428 is loaded onto the anchor driver 426. The tool 420 is then reintroduced into the anchor catheter 440, and the second anchor is deployed. These steps are repeated until all of the anchors 428 have been deployed. Alternatively, the entire deployment tool 420, including the anchor catheter 440, may be removed from the body and subsequently reintroduced after being provided with another anchor 428. In a further alternative, the tool 420 is configured to simultaneously hold a plurality of anchors 428, and to deploy them one at a time (configuration not shown).

FIGS. 24A-24C are sectional views of steps in utilizing an exemplary tissue anchoring catheter 440 through the sleeve-like annuloplasty ring 400 to install one of the anchors 428. The anchoring catheter 440 is similar to the anchoring catheter described above with respect to FIGS. 3-4, with an assembly of components on the distal end thereof for regulating the pressure of the catheter against tissue. The components include a distal tubular housing 452 that slides axially within a tubular housing frame 454 that is in turn surrounded by a thin tubular cover 456. A distal end of an elongated pusher 460 engages via a coil spring 462 a proximal end of the housing frame 454. The coil spring 462 is centered on a short radially recessed portion 463 of the pusher 460 and extends between the pusher and a proximal end of the tubular housing 452. The distal end of the pusher 460 may be fixed with respect to the housing frame 454, as well as to the proximal end of the coil spring 462.

The tubular housing 452 includes an enlarged distal tip 464 formed as a thick echogenic ring, such as by providing changes in diameter, chamfers or knurling on an exterior periphery thereof, as shown. (As explained above, "echogenic" does not strictly refer to the sound reflective properties of the distal tip 464, but to its ability to effectively reflect various types of waves, such as the X-rays used in fluoroscopy.)

After positioning the next segment of the annuloplasty ring 400 to be installed against the annulus, as seen in FIG. 24A, the operator advances the catheter 440 and connected housing frame 454 to compress the spring 462, as seen in FIG. 24B. Although not shown, the pusher 460 preferably extends back to a proximal handle and an actuator which slides it forward and backwards, or is coupled to a secondary shaft (not shown) which extends proximally to the handle. At the point where the spring 462 is fully compressed (or least compressed to a desired amount), a distal portion of the housing frame 454 comes into close proximity with the thick distal tip 464 of the tubular housing 452.

As with the earlier-described catheter, a schematic image of the appearance of the distal assembly of components in this sequence is seen in FIGS. 10A and 10B, wherein the relatively thick housing frame 454 (54) shows up as a dark rectangular mass that eventually moves into close proximity with the relatively large mass distal tip 464 (64) that also shows up as dark on the image display. The remainder of the tubular components have lesser wall thicknesses, and in contrast show up less distinctly on the image display. The operator can thus tell when the spring 462 has been fully compressed (or least compressed to the requisite amount), and the desired compressive force for anchor deployment has been reached. Several alternative configurations of a distal assembly of components on the catheter which affords good visibility using an imaging sensor/display are disclosed herein, some of which are discussed above with regards to FIGS. 11 and 12.

As mentioned above, the coil spring 462 may be completely compressed, as shown, though this is not strictly necessary and the spring may be only partly compressed. In either case, compression of the spring 462 at the moment when the distal end of the housing frame 454 reaches the distal tip 464 provides a calibrated and desirable compressive force of the catheter against the tissue. That is, the spring constant is calibrated so that linear compression to the extent seen in FIG. 24B produces a contact force which will ensure that the tissue anchor 428 will properly embed within the tissue once advanced from the tubular housing 452. As will be understood, the particular contact force for which the spring 462 is calibrated depends on a number of factors such as the size and configuration of the tissue anchor 428, the character of the tissue into which anchor is embedded, and the subsequent forces expected to be imparted to the annuloplasty ring 400 once fully implanted, among others. In an exemplary embodiment, the illustrated tissue anchor 428 is properly anchored within the annulus tissue when expelled from the catheter that exerts a contact force against the tissue of between 0.5-2.0 N, and more preferably about 1.0 N.

Subsequently, as seen in FIG. 24C, the operator separately advances the flexible shaft 424 of the tool 420 through a lumen in the pusher 460. Although not shown, further advancement of the tissue anchor 428 causes it to pass through the fabric wall of the sleeve-like annuloplasty ring 400 and contact the tissue, and it can then be rotated by the shaft 424 and anchor driver 426 to cause the corkscrew-like tine to advance into the tissue. Because of the compressive force imparted by the catheter 440 on the tissue, an equal and opposite reactive force from the tissue is established. The tissue anchor 428 encounters this force upon emerging from the distal tip 464, and consequently deploys in the expected manner.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A system for ensuring secure anchoring of a cardiac tissue anchor within cardiac tissue in a patient's body, comprising:

a cardiac tissue anchor deployment system including a proximal handle connected to an elongated flexible tube having a lumen within which translates an elongated flexible tissue anchor tool with a distal tissue anchor thereon suitable for piercing and anchoring into cardiac tissue;

a tissue contact indicator assembly configured to be visible from outside the body on a display for an imaging sensor, the indicator assembly being located adjacent a distal end of the flexible tube and having a distal tubular housing arranged to slide proximally within the flexible tube that in a first position presents a first visual image on the display for the imaging sensor prior to contact between the distal end of the flexible tube and tissue, and presents a second visual image distinct from the first visual image after moving to a second position when a predetermined force of between 0.5-2.0 N is applied between the distal end of the flexible tube and the cardiac tissue, the predetermined force being calibrated to ensure that the tissue anchor securely embeds into the cardiac tissue when the tissue anchor tool is subsequently advanced, wherein the tubular housing has at least one cantilevered section on a proximal end having an outwardly-directed retention tab, and wherein an exterior diameter of the proximal end of the tubular housing fits closely within a lumen of the distal end of the flexible tube, and each retention tab is biased to flex outward into an axial slot in the flexible tube.

2. The system of claim 1, wherein the tubular housing has a relatively thin-walled body and a distal ring that is thicker than the thin-walled body and consequently more visible to the imaging sensor, and the flexible tube having a tubular housing frame at a distal end with a relatively thick wall that is visible to the imaging sensor, wherein proximal movement of the distal tubular housing causes the distal ring to move into proximity with the tubular housing frame and form the second visual image.

3. The system of claim 2, wherein the distal ring exhibits at least one chamfer or an outer surface that is uneven for greater visibility to the imaging sensor.

4. The system of claim 2, further including a spring positioned between the tubular housing and the flexible tube which determines the predetermined force.

5. The system of claim 4, further including a tensioner positioned intermediate the tissue contact indicator assembly and the proximal handle which exerts a proximal force on the elongated tissue anchor tool, the tissue anchor having a size that interferes with a portion of the tubular housing so as to retract the tubular housing within the flexible tube.

6. The system of claim 1, wherein the tubular housing has a first radiopaque band thereon that is more visible to the imaging sensor than a remainder of the tubular housing, and the flexible tube having a second radiopaque band thereon, wherein the first visual image shows the first and second radiopaque bands spaced a first distance apart and the second visual image shows the first and second radiopaque bands closer together than the first distance.

7. The system of claim 1, further including a locking member that prevents movement of the tubular housing and is manually disengaged using an actuator on the proximal handle, the locking member holding the outwardly-directed retention tab on the cantilevered section of the tubular housing from flexing outward into the axial slot in the flexible tube.

8. The system of claim 1, wherein the retention tab on the tubular housing has a proximal ramp that permits the cantilevered section to flex inward upon insertion of the tubular housing into the distal end of the flexible tube and the distal end of the retention tab has a radial face which engages a distal end of the axial slot so as to retain the tubular housing within the flexible tube.

9. The system of claim 1, wherein the elongated tissue anchor tool is detachable from the tissue anchor.

10. The system of claim 1, wherein the tissue anchor is selected from the group consisting of:
 a plurality of distally-directed sharp tines having an outward elastic bias such that they curl outward upon release from a surrounding constraint, and
 a corkscrew-like tine.

11. A system for ensuring secure anchoring of a cardiac tissue anchor within cardiac tissue in a patient's body, comprising:
 a cardiac tissue anchor deployment system including a proximal handle connected to an elongated flexible tube having a lumen within which translates an elongated flexible tissue anchor tool with a distal tissue anchor thereon suitable for piercing and anchoring into cardiac tissue;
 a tissue contact force regulator assembly adjacent a distal end of the flexible tube including a distal tubular housing arranged to slide proximally within a distal end of the flexible tube, the tissue contact force regulator having a pusher shaft that is in a first position prior to contact between the tubular housing and cardiac tissue and is coupled to move with the tissue anchor tool, the tissue contact force regulator assembly including a spring positioned between the pusher shaft and the tubular housing, wherein after contact of the tubular housing with cardiac tissue, initial advancement of the pusher shaft to a second position displaces the tissue anchor tool to a distal end of the tubular housing and compresses the spring to apply a predetermined force of between 0.5-2.0 N between the distal end of the flexible tube and the cardiac tissue, wherein further advancement of the tissue anchor tool embeds the tissue anchor into the cardiac tissue, and wherein the predetermined force is calibrated to ensure that the tissue anchor securely embeds into the cardiac tissue when the tissue anchor tool is advanced, wherein the tubular housing has at least one cantilevered finger on a proximal end having an outwardly-directed retention tab, and wherein an exterior diameter of the proximal end of the tubular housing fits closely within a lumen of the distal end of the flexible tube, and the retention tab is held flexed inward to interfere with and prevent distal movement of the pusher.

12. The system of claim 11, wherein the spring is fully compressed when the pusher shaft is in the second position and remains stationary during further advancement of the tissue anchor tool.

13. The system of claim 11, wherein the tubular housing has a relatively thin-walled body and a distal ring that is thicker than the thin-walled body and consequently more visible on a display for an imaging sensor located outside the body, the tubular housing being arranged to slide proximally within the flexible tube, and the flexible tube having a tubular housing frame at a distal end with a relatively thick wall that is visible to the imaging sensor, wherein proximal movement of the distal tubular housing causes the distal ring to move into proximity with the tubular housing frame that is visible from outside the body on the display for the imaging sensor.

14. The system of claim 13, further including a tensioner positioned intermediate the tissue contact force regulator assembly and the proximal handle which exerts a proximal force on the elongated tissue anchor tool, the tissue anchor having a size that interferes with a portion of the tubular housing so as to retract the tubular housing within the flexible tube.

15. The system of claim 13, further including a locking member that prevents movement of the tubular housing and is manually disengaged using an actuator on the proximal handle, the locking member comprising a lockout wire that holds the outwardly-directed retention tab on the cantilevered section of the tubular housing from flexing outward.

16. The system of claim 11, wherein the elongated tissue anchor tool comprises a flexible rail affixed to the tissue anchor.

17. The system of claim 11, wherein the elongated tissue anchor tool is detachable from the tissue anchor.

18. The system of claim 11, wherein the tissue anchor is selected from the group consisting of:
 a plurality of distally-directed sharp tines having an outward elastic bias such that they curl outward upon release from a surrounding constraint, and
 a corkscrew-like tine.

19. The system of claim 11, wherein the spring is a coil spring positioned around a narrow distal end of the pusher shaft that engages the flexible tube and compresses as the narrow distal portion passes through the flexible tube.

20. The system of claim 11, further including a guide balloon positioned around the distal end of the flexible tube that helps prevent entanglement of the distal end of the flexible tube with anatomical structures.

\* \* \* \* \*